US010274693B2

(12) United States Patent
Kobayashi et al.

(10) Patent No.: US 10,274,693 B2
(45) Date of Patent: Apr. 30, 2019

(54) MEDICAL OBSERVATION DEVICE AND LENS BARREL OF MEDICAL OBSERVATION DEVICE

(71) Applicant: Sony Corporation, Tokyo (JP)

(72) Inventors: Keishi Kobayashi, Kanagawa (JP); Hiroyuki Mori, Kanagawa (JP); Takashi Kato, Kanagawa (JP); Motoshige Itou, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/550,665

(22) PCT Filed: Dec. 28, 2015

(86) PCT No.: PCT/JP2015/086485
§ 371 (c)(1),
(2) Date: Aug. 11, 2017

(87) PCT Pub. No.: WO2016/132656
PCT Pub. Date: Aug. 25, 2016

(65) Prior Publication Data
US 2018/0031797 A1 Feb. 1, 2018

(30) Foreign Application Priority Data

Feb. 18, 2015 (JP) .................. 2015-029546

(51) Int. Cl.
G02B 7/02 (2006.01)
H04N 5/232 (2006.01)
(Continued)

(52) U.S. Cl.
CPC ............ *G02B 7/021* (2013.01); *A61B 90/361* (2016.02); *G02B 1/04* (2013.01); *G02B 7/003* (2013.01);
(Continued)

(58) Field of Classification Search
CPC . G02B 7/021; G02B 7/10; G02B 1/04; G02B 7/04; G02B 7/02; H04N 5/232; H04N 5/225; A61B 90/361
(Continued)

(56) References Cited

FOREIGN PATENT DOCUMENTS

JP 60-069955 4/1985
JP 61-259599 11/1986
(Continued)

*Primary Examiner* — Tuyen Tra
(74) *Attorney, Agent, or Firm* — Michael Best & Friedrich LLP

(57) ABSTRACT

To realize weight reduction and ensure favorable performance of an imaging element.
A lens barrel of a medical observation device includes: a barrel unit including an imaging optical system configured to acquire an image of an object, and a housing in which the imaging optical system is disposed; and an element unit including an imaging element configured to photoelectrically convert the image of the object acquired by the imaging optical system, and an element holder configured to hold the imaging element, in which the housing is made of a resin material, and the element holder is made of a material different from that of the housing. With this configuration, the housing in which the imaging optical system is disposed is made of the resin material, and the element holder configured to hold the imaging element is made of the material different from that of the housing. Thus, weight reduction can be realized while favorable performance of the imaging element can be ensured.

9 Claims, 18 Drawing Sheets

(51) Int. Cl.
    *A61B 90/00*     (2016.01)
    *G02B 1/04*      (2006.01)
    *G02B 7/10*      (2006.01)
    *G02B 7/00*      (2006.01)
    *G02B 7/08*      (2006.01)
    *H04N 5/225*     (2006.01)

(52) U.S. Cl.
    CPC ............... *G02B 7/028* (2013.01); *G02B 7/08* (2013.01); *G02B 7/10* (2013.01); *H04N 5/2254* (2013.01); *H04N 5/232* (2013.01)

(58) Field of Classification Search
    USPC .......................... 359/823, 824, 642, 811, 819
    See application file for complete search history.

(56) References Cited

FOREIGN PATENT DOCUMENTS

| | | |
|---|---|---|
| JP | H06-311310 | 11/1994 |
| JP | 2002-301025 A | 10/2002 |
| JP | 2004-081231 A | 3/2004 |
| JP | 2005-006769 A | 1/2005 |
| JP | 2007-167125 A | 7/2007 |
| JP | 2011-104068 A | 6/2011 |
| WO | WO-2014/203983 A1 | 12/2014 |

MEDICAL OBSERVATION DEVICE AND LENS BARREL OF MEDICAL OBSERVATION DEVICE

TECHNICAL FIELD

The present technology relates to a technical field for a medical observation device used in a medical field and including a barrel unit having an imaging optical system configured to acquire an image of an object and an element unit including an imaging element and for a lens barrel of the medical observation device.

CITATION LIST

Patent Document

Patent Document 1: Japanese Patent Application Laid-Open No. 2004-81231
Patent Document 2: Japanese Patent Application Laid-Open No. 2011-104068

BACKGROUND ART

For example, for practice such as operation, medical treatment, and examination in medical institutions such as a hospital, a medical observation device has been proposed, which is configured to enhance a treatment efficiency by observation of an affected area of a patient. Such a medical observation device is attached to, e.g., a tip end portion of a robot arm, and is used such that the arm is operated to set the medical observation device to a necessary direction or angle. This allows observation of the affected area of the patient from a desired direction. Alternatively, the medical observation device is used with a practitioner gripping the medical observation device. An image or a video acquired by the medical observation device is displayed on a display section such as a monitor or a display.

This medical observation device includes, for example, a medical observation device including an imaging optical system configured to acquire an image of an object and an imaging element configured to photoelectrically convert the image of the object acquired by the imaging optical system. Such a medical observation device is configured such that the imaging optical system is disposed in a housing, the imaging element is held by an element holder, and the housing and the element holder are linked together (see, e.g., Patent Documents 1 and 2).

SUMMARY OF THE INVENTION

Problems to be Solved by the Invention

Meanwhile, the medical observation device is used for the practice such as operation, medical treatment, and examination, and therefore, sterilization processing called "autoclaving" is performed before treatment. Autoclaving is performed in a manner that the medical observation device is left for about 10 minutes under a high temperature of equal to or higher than 100° C., for example. For this reason, the medical observation device needs to be configured to resist high temperature. However, if the housing is made of a metal material to ensure heat resistance, this poses a problem for weight reduction of the medical observation device. In particular, in a case where the medical observation device is gripped by the practitioner upon use, it is extremely important to reduce the weight.

For these reasons, the housing in which the imaging optical system and the element holder configured to hold the imaging element are preferably made of a material which exhibits heat resistance against autoclaving and by which weight reduction can be realized.

Meanwhile, since the imaging element is held being attached to the element holder with an adhesive etc., the element holder needs to be made of a material suitable for the adhesive etc. for ensuring favorable performance of the imaging element.

For these reasons, a medical observation device and a lens barrel of the medical observation device according to the present technology are intended to overcome the above-described problems and to realize weight reduction while ensuring favorable performance of an imaging element.

Solutions to Problems

First, a lens barrel of a medical observation device according to the present technology includes: a barrel unit including an imaging optical system configured to acquire an image of an object, and a housing in which the imaging optical system is disposed; and an element unit including an imaging element configured to photoelectrically convert the image of the object acquired by the imaging optical system, and an element holder configured to hold the imaging element, in which the housing is made of a resin material, and the element holder is made of a material different from that of the housing.

With this configuration, the housing in which the imaging optical system is disposed is made of the resin material, and the element holder configured to hold the imaging element is made of the material different from that of the housing.

Second, in the lens barrel of the medical observation device, it is desirable that one or more lenses are provided at the imaging optical system, a movable frame is provided, which is configured to hold at least one of the lenses and move in an optical axis direction, and the movable frame is made of a resin material.

With this configuration, the movable frame configured to hold the lens and move in the optical axis direction is made of the resin material.

Third, in the lens barrel of the medical observation device, it is desirable that autofocusing is performed in such a manner that the at least one of the lenses held by the movable frame is moved in the optical axis direction in association with movement of the movable frame.

With this configuration, autofocusing is performed in such a manner that the lens is moved in the optical axis direction in association with movement of the movable frame made of the resin material.

Fourth, in the lens barrel of the medical observation device, it is desirable that a drive shaft whose axial direction is along the optical axis direction, and a guide shaft disposed parallel to the drive shaft are further provided, the movable frame is supported by the drive shaft and the guide shaft, and the movable frame is, using drive force transferred from the drive shaft, guided and moved by the guide shaft.

With this configuration, direct acting type driving is performed, in which the movable frame and the lens are moved in the optical axis direction by the drive force transferred from the drive shaft.

Fifth, in the lens barrel of the medical observation device, it is desirable that at least two eccentric pins for positioning of the barrel unit and the element unit in a plane perpendicular to the optical axis direction is further provided, at least two pin insertion holes are formed at the barrel unit, at least two pin insertion through-holes are formed at the element unit, a portion of each eccentric pin is inserted into a corresponding one of the pin insertion holes, and another portion of each eccentric pin is inserted into a corresponding one of the pin insertion through-holes, at least one of the eccentric pins is rotated in a direction about an axis such that a position of the element unit with respect to the barrel unit is adjusted, and at least one of the pin insertion through-holes is formed in an elongated-hole shape.

With this configuration, when one of the barrel unit or the element unit displaces relative to the other one of the barrel unit or the element unit due to expansion or contraction of the barrel unit or the element unit caused by external environment, displacement of the barrel unit or the element unit according to a change in external environment is allowed.

Sixth, in the lens barrel of the medical observation device, it is desirable that each eccentric pin includes an insertion shaft portion to be inserted into a corresponding one of the pin insertion through-hole, and an eccentric shaft portion which is to be inserted into a corresponding one of the pin insertion holes and which is provided eccentric with respect to the insertion shaft portion, and an eccentric amount of the eccentric shaft portion with respect to the insertion shaft portion is identical among all of the eccentric pins.

With this configuration, the same eccentric pins can be used as all of the eccentric pins.

Seventh, in the lens barrel of the medical observation device, it is desirable that in a state in which positioning of the barrel unit and the element unit is made by the eccentric pins, the barrel unit and the element unit are, in the optical axis direction, linked together with a fastening screw.

With this configuration, the barrel unit and the element unit are linked together by the fastening screw with positioning of the barrel unit and the element unit being held.

Eighth, in the lens barrel of the medical observation device, it is desirable that a retainer spring configured to push the element unit against the barrel unit is supported on the fastening screw.

With this configuration, the retainer spring expands/contracts when the barrel unit or the element unit expands or contracts due to the change in external environment.

Ninth, in the lens barrel of the medical observation device, it is desirable that a screw hole into which the fastening screw is to be screwed is formed at the barrel unit, a screw insertion hole into which the fastening screw is to be inserted is formed at the element unit, and a diameter of the screw insertion hole is larger than that of the fastening screw.

With this configuration, the fastening screw displaces relative to the screw insertion hole when the barrel unit or the element unit expands or contracts due to the external environment.

A medical observation device according to the present technology includes: a barrel unit including an imaging optical system configured to acquire an image of an object, and a housing in which the imaging optical system is disposed; and an element unit including an imaging element configured to photoelectrically convert the image of the object acquired by the imaging optical system, and an element holder configured to hold the imaging element, in which the housing is made of a resin material, and the element holder is made of a material different from that of the housing.

With this configuration, in the lens barrel, the housing in which the imaging optical system is disposed is made of the resin material, and the element holder configured to hold the imaging element is made of the material different from that of the housing.

Effects of the Invention

According to the present technology, the housing in which the imaging optical system is disposed is made of the resin material while the element holder configured to hold the imaging element is made of the material different from that of the housing. Thus, weight reduction can be realized while favorable performance of the imaging element can be ensured.

Note that effects described in the present specification have been set forth merely as examples, and are not limited. Other effects may be provided.

MODE FOR CARRYING OUT THE INVENTION

A mode for carrying out the present technology will be described below with reference to the attached drawings.

A medical observation device of the mode described below is a medical observation device configured so that a moving image or a still image can be shot, and is configured such that a direction connecting between a lens and an imaging element is an optical axis direction.

In description below, the optical axis direction indicates a front-to-back direction, and predetermined directions perpendicular to the optical axis direction respectively indicate an upper-to-lower direction and a right-to-left direction. Moreover, description will be made in a state in which an object side is a front side and a direction in which an object image is taken is a back side.

Note that the front-to-back, upper-to-lower, and right-to-left directions described below are set forth for the sake of description, and implementation of the present technology is not limited to these directions.

Moreover, a lens group described below may include a lens group having one or more lenses, and a lens group having these one or more lenses and other optical elements such as a diaphragm and an iris.

[Outline Configuration of Medical Observation Device]

Figure 1:
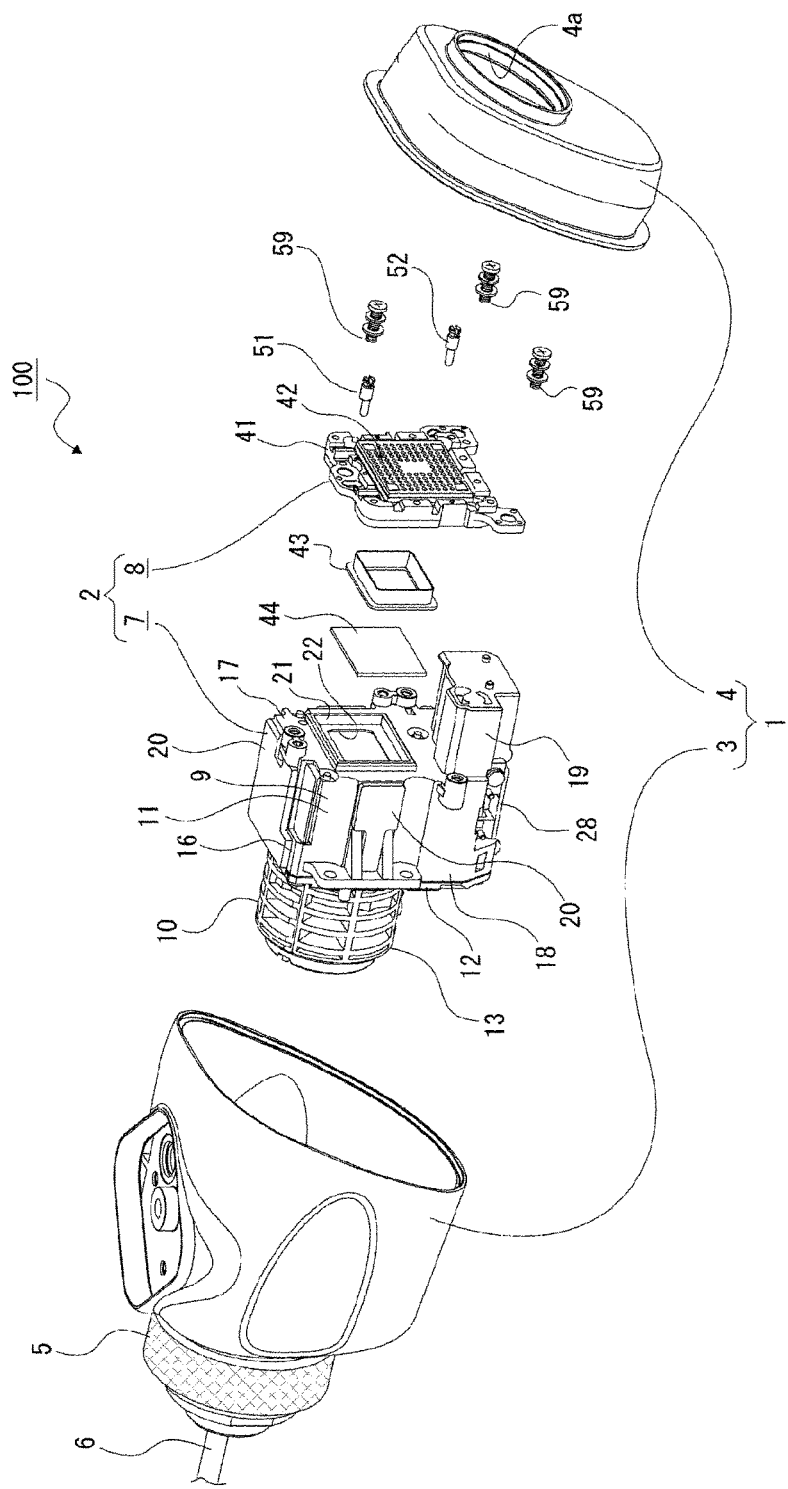
FIG. 1 illustrates, together with FIGS. 2 to 18, a mode of a medical observation device and a lens barrel of the medical observation device according to the present technology, and is an exploded perspective view of the medical observation device.
Figure 2:
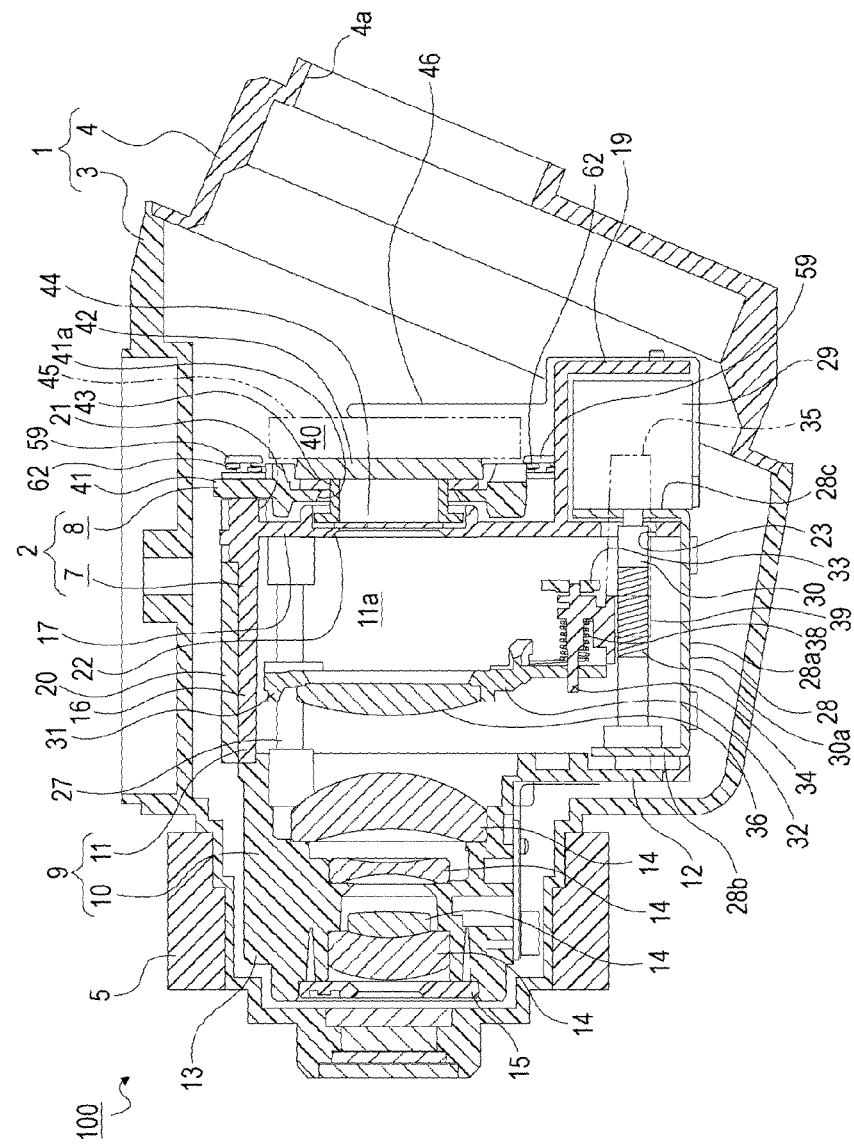
FIG. 2 is a cross-sectional view of the medical observation device.
Figure 3:
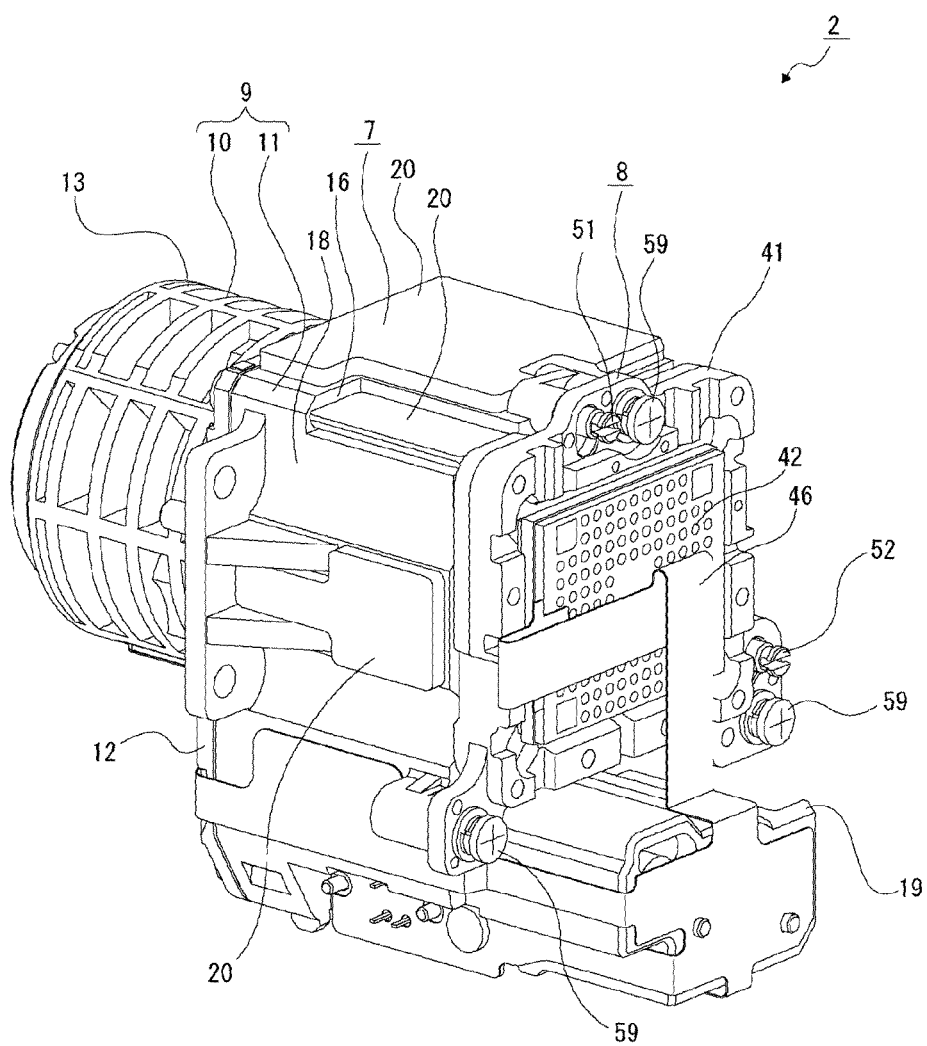
FIG. 3 is a perspective view of the lens barrel.
Figure 4:
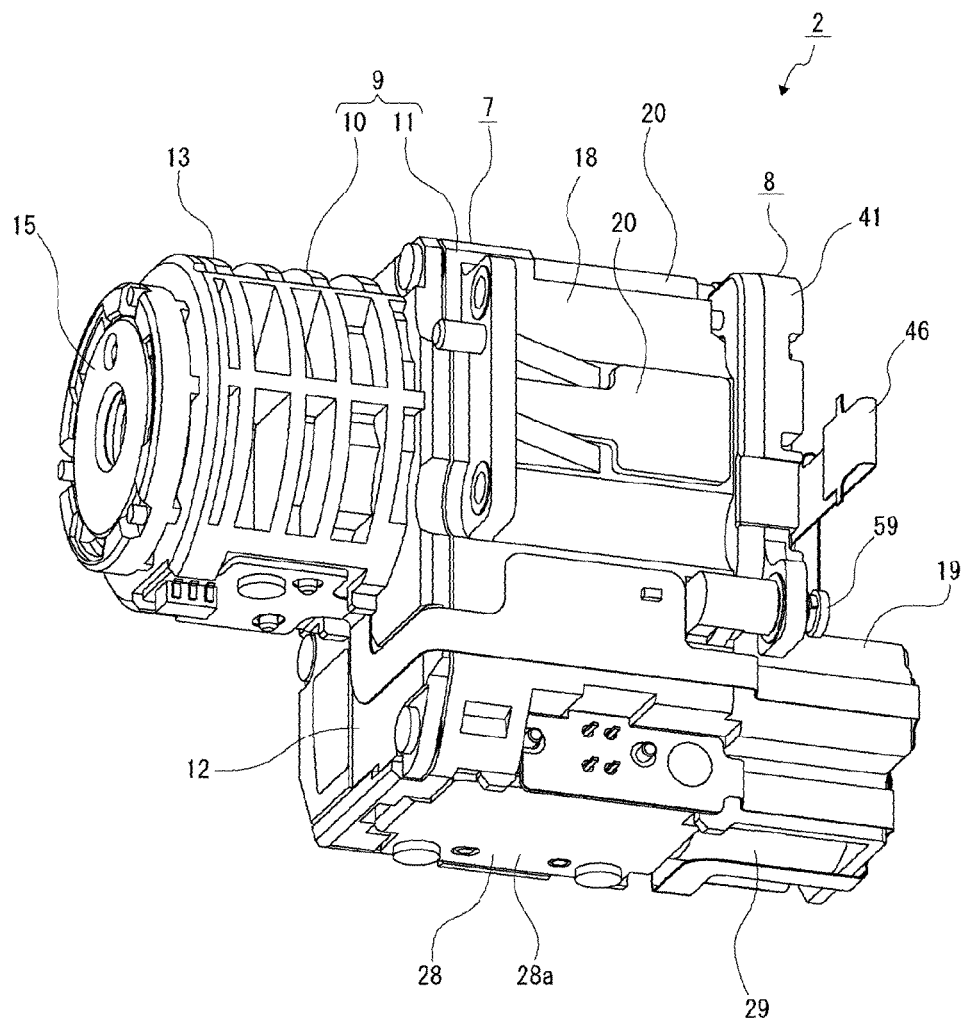
FIG. 4 is a perspective view of the lens barrel from a direction different from that of FIG. 3.

First, an outline configuration of the medical observation device will be described (see FIGS. 1 and 2).

A medical observation device 100 is configured such that a lens barrel 2 is disposed in an outer casing 1. The outer casing 1 is made of a metal material such as titanium. The outer casing 1 includes a recessed case body 3 opening on the back side, and a shallow recessed cover body 4 opening on the front side. The outer casing 1 is configured such that the case body 3 and the cover body 4 are linked together in the front-to-back direction. The outer casing 1 has the function of protecting the lens barrel 2, as well as functioning as a grip portion gripped by a practitioner.

A manual focus ring 5 is rotatably supported at a front end portion of the case body 3. The manual focus ring 5 is manually operated so that a movable frame and a focus lens as described later can move in the optical axis direction (the front-to-back direction) to manually perform manual focusing.

An insertion portion 6 in which a not-shown relay lens is disposed is attached to the front end portion of the case body 3. The insertion portion 6 is inserted into, e.g., an affected area of a patient, and an image or a video of the affected area etc. is shot via the insertion portion 6 by the lens barrel 2. The shot image or video is displayed on a not-shown monitor, and the practitioner performs treatment while checking the image or the video displayed on the monitor.

An insertion hole 4a is formed at a back surface portion of the cover body 4. A not-shown cable for power supply to the lens barrel 2 or transmission/reception of a signal for the image or the video formed by the lens barrel 2 is inserted into the insertion hole 4a.

[Configuration of Lens Barrel]

The lens barrel 2 is configured such that a barrel unit 7 and an element unit 8 are linked together in the front-to-back direction (see FIGS. 3 to 6).

The barrel unit 7 includes a housing 9 and each of necessary portions such as an imaging optical system having a plurality of lenses arranged inside and outside the housing 9 as described later. The housing 9 is made of a resin material exhibiting excellent heat resistance, such as polyether sulphone (PES), and contains carbon. The housing 9 is configured such that a front cabinet 10 and a back cabinet 11 are linked together in the front-to-back direction.

The front cabinet 10 includes a plate-shaped base plate portion 12 facing the front-to-back direction, and a lens holding portion 13 protruding forward from a portion of the base plate portion 12 excluding a lower end portion thereof. The front cabinet 10 is formed in such a substantially cylindrical shape that the lens holding portion 13 penetrates the front cabinet 10 in the front-to-back direction.

A plurality of lenses 14 are arranged in the optical axis direction (the front-to-back direction) in the lens holding portion 13, and are held by the lens holding portion 13. A diaphragm 15 is held at a front end portion of the lens holding portion 13.

The back cabinet 11 is formed in a box shape opening on the front and lower sides. The back cabinet 11 includes a top surface portion 16 facing the upper-to-lower direction, a back surface portion 17 facing the front-to-back direction, side surface portions 18 facing the right-to-left direction, and an arrangement portion 19 protruding backward from a lower end portion of the back surface portion 17. The arrangement portion 19 is formed in a box shape opening on the lower side.

Heat sinks 20 are attached respectively to outer surfaces of the top surface portion 16 and the side surface portions 18. For example, two heat sinks 20 are attached to the top surface portion 16, and a single heat sink 20 is attached to each side surface portion 18. Heat is released from the heat sinks 20, and therefore, a temperature increase at each portion of the housing 9 is suppressed in a temperature increase. Particularly in driving of the element unit 8, the amount of heat transferred from the later-described imaging element of the element unit 8 to the back cabinet 11 is great, and a temperature increase at each portion of the housing 9 is suppressed by heat release from the heat sinks 20 in driving of the element unit 8 while a stable driving state of the imaging element is ensured.

Note that the housing 9 contains carbon, and therefore, high heat conductivity of the housing 9 is ensured while the strength of the housing 9 is improved.

An arrangement recessed portion 21 opening on the back side is formed on an upper end side of the back surface portion 17, and a transmission hole 22 is formed to penetrate a portion forming the arrangement recessed portion 21 in the front-to-back direction. A communication hole 23 is formed at a position closer to a lower end of the back surface portion 17, and allows communication between an internal space 11a as a space of the housing 9 on the front side of the back surface portion 17 and an internal space of the arrangement portion 19.

Screw holes 24 are formed at an outer peripheral portion of the back surface portion 17. The screw holes 24 open on the back side.

A first pin insertion hole 25 and a second pin insertion hole 26 each opening on the back side are formed at the back surface portion 17. The first pin insertion hole 25 is formed in a circular shape, and is positioned at an upper end portion of the back surface portion 17, for example. The second pin insertion hole 26 is also formed in a circular shape, and is positioned at one side portion of the back surface portion 17 below the first pin insertion hole 25, for example.

Figure 6:
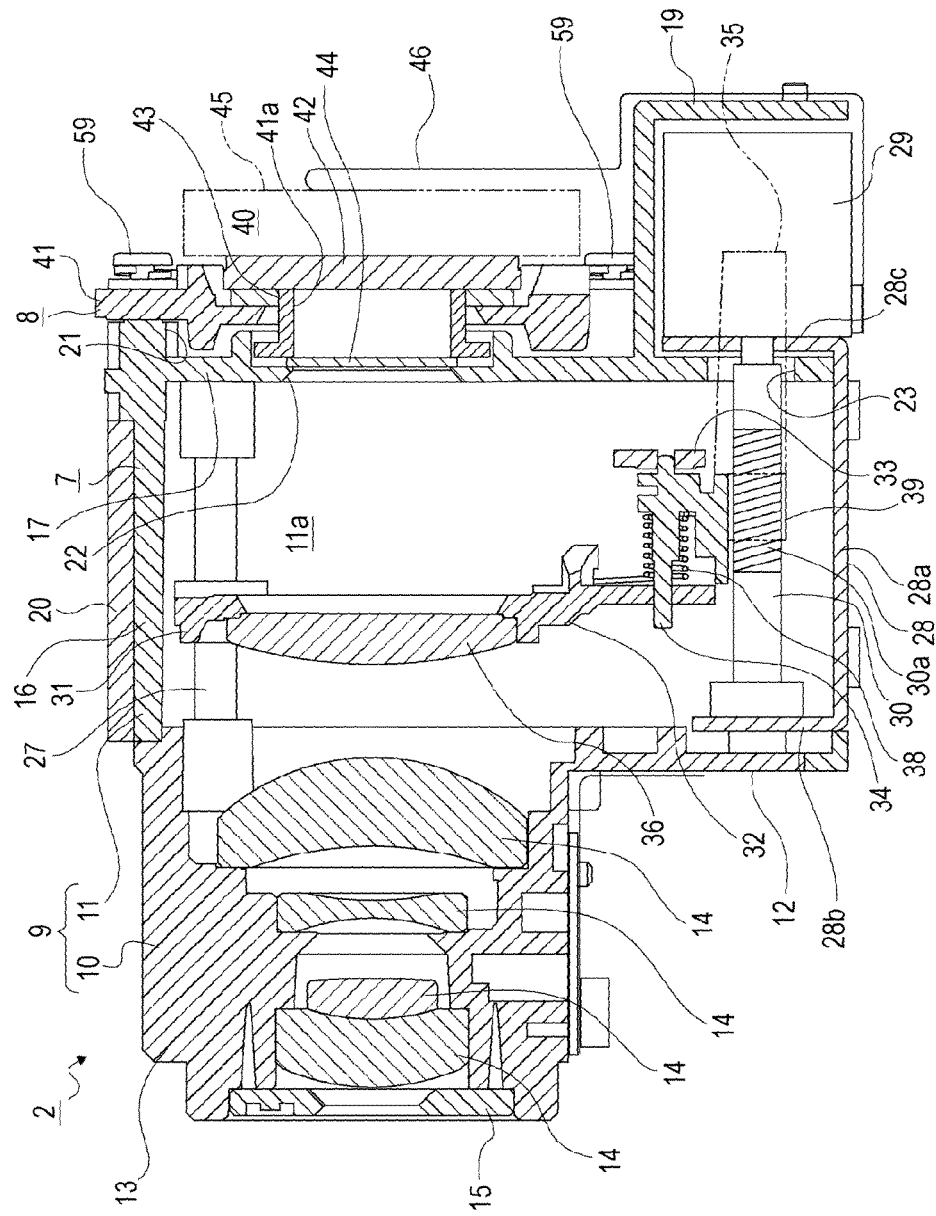
FIG. 6 is a cross-sectional view of the lens barrel.
Figure 7:
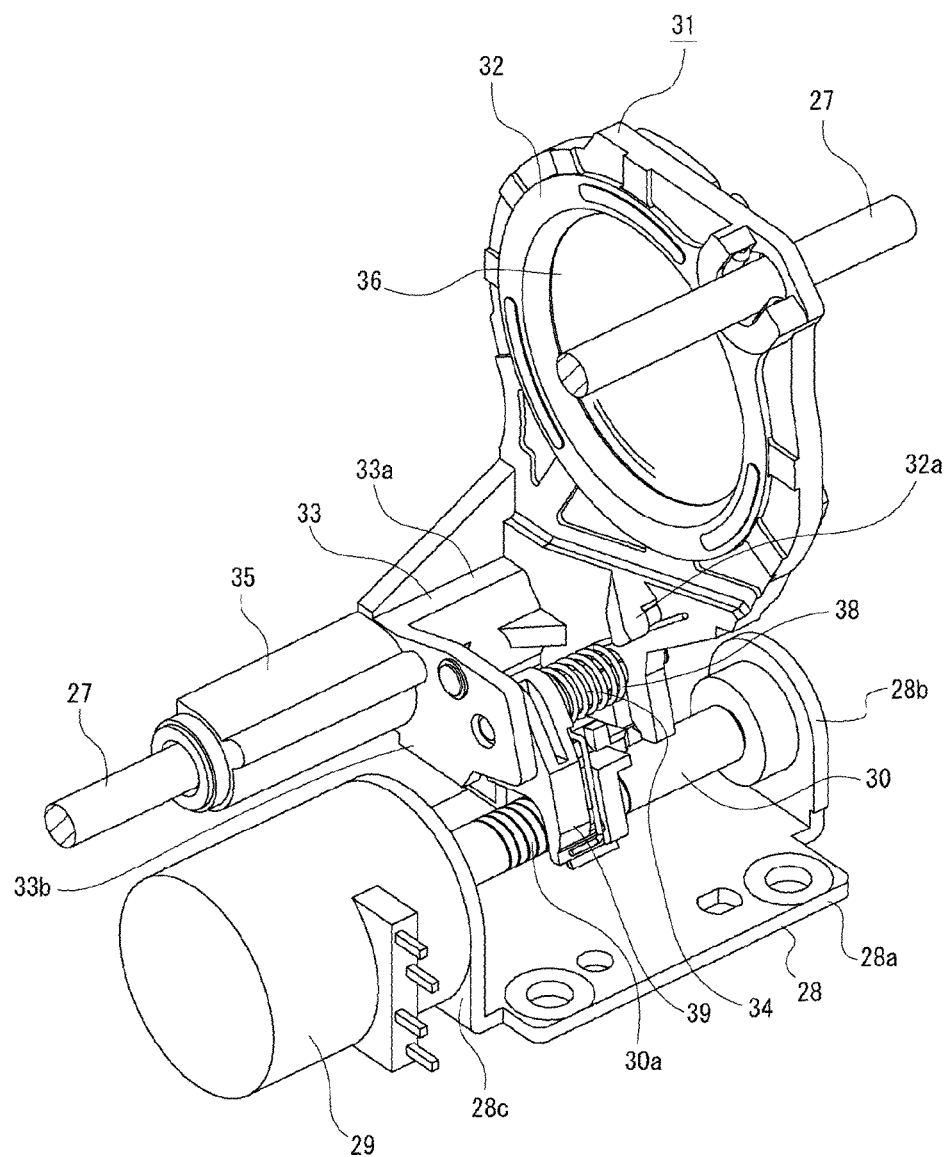
FIG. 7 is an enlarged perspective view of a movable frame etc.
Figure 8:
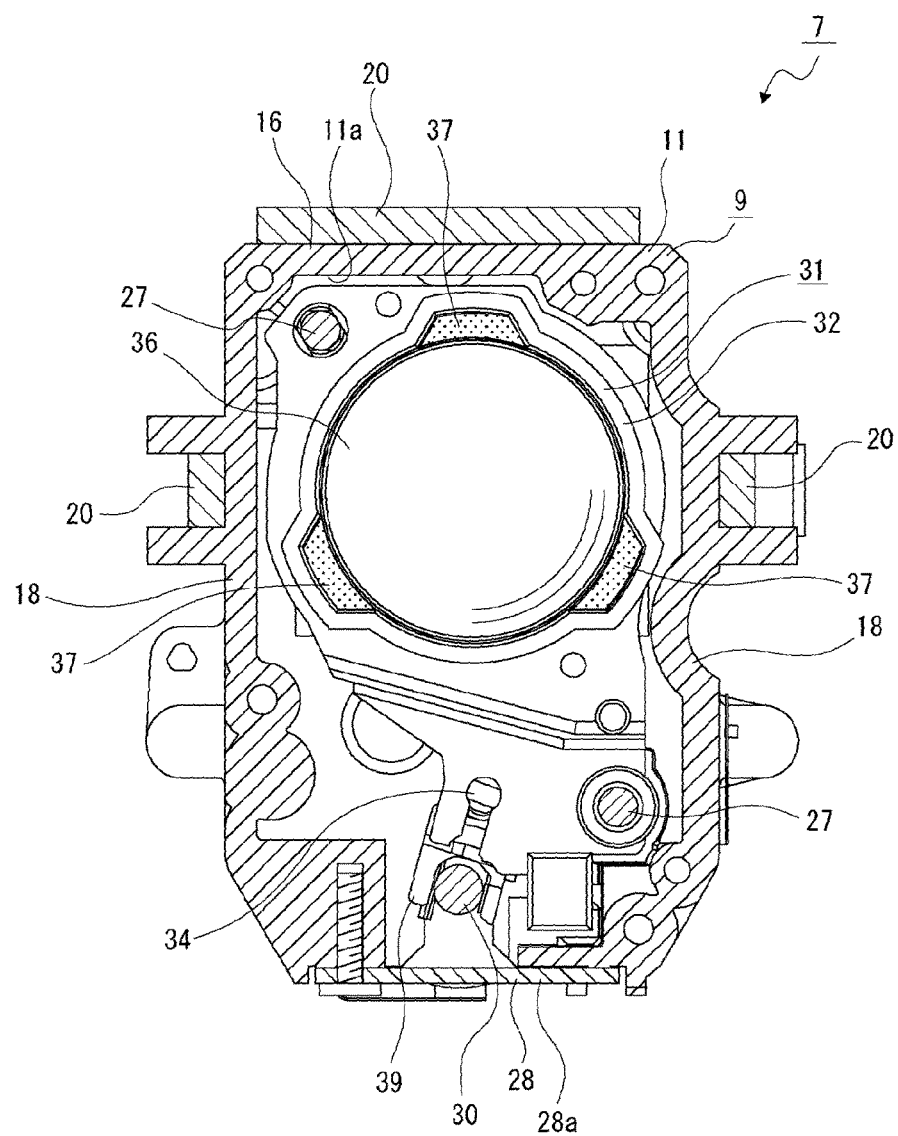
FIG. 8 is a front view of the movable frame etc. with a partial cross-sectional view.

Guide shafts 27 made of a metal material are arranged in the internal space 11a of the back cabinet 11 (see FIGS. 6 to 8). The guide shafts 27 are arranged respectively at upper and lower end portions of the internal space 11a, and both end portions of each guide shaft 27 in an axis direction thereof are attached respectively to the lens holding portion 13 and the back surface portion 17.

An attachment plate 28 is attached to a lower end portion of the back cabinet 11. The attachment plate 28 includes a coupling surface portion 28a facing the upper-to-lower direction and extending in the upper-to-lower direction, a support surface portion 28b protruding upward from a front end portion of the coupling surface portion 28a, and an attachment surface portion 28c protruding upward from a back end portion of the coupling surface portion 28a. The attachment surface portion 28c is positioned at a front end portion in the arrangement portion 19, and the support surface portion 28b is positioned at a front end portion in the internal space 11a.

A drive motor 29 is attached to a back surface of the attachment surface portion 28c of the attachment plate 28. The drive motor 29 is, e.g., a stepping motor, and is disposed at the arrangement portion 19. A drive shaft (an output shaft) of the drive motor 29 is provided as a lead screw 30. The lead screw 30 is positioned in the internal space 11a with the lead screw 30 penetrating the attachment surface portion 28c. A front end portion of the lead screw 30 is supported by the support surface portion 28b. The lead screw 30 is made of a metal material.

The movable frame 31 is slidably supported by the guide shafts 27. The movable frame 31 is made of a resin material exhibiting excellent heat resistance, such as polyether sulphone. The movable frame 31 includes a lens holding portion 32 facing the front-to-back direction, a coupling protrusion 33 protruding backward from a lower end portion of the lens holding portion 32, a support shaft portion 34 linked to the coupling protrusion 33, and a sleeve portion 35 protruding backward from the coupling protrusion 33.

A portion of the lens holding portion 32 excluding the lower end portion thereof is formed in an annular shape. At the annular portion of the lens holding portion 32, the focus lens 36 made of a glass material is held, for example. A spring support piece 32a protruding backward is provided at a position closer to a lower end of the lens holding portion 32.

The coupling protrusion 33 includes a protruding portion 33a protruding backward from the lens holding portion 32, and a linking protrusion 33b laterally protruding from a back end portion of the protruding portion 33a.

The support shaft portion 34 is formed in a round shaft shape extending in the front-to-back direction. A front end portion of the support shaft portion 34 is linked to the lower end portion of the lens holding portion 32, and a back end portion of the support shaft portion 34 is linked to the linking protrusion 33b.

The sleeve portion 35 is formed in a substantially cylindrical shape whose axial direction is along the front-to-back direction, and protrudes backward from the protruding portion 33a.

The movable frame 31 is configured such that an upper end portion of the lens holding portion 32 and the sleeve portion 35 are each slidably supported by a corresponding one of the guide shafts 27, and can be guided by the guide shafts 27 to move in the optical axis direction (the front-to-back direction) together with the focus lens 36.

Figure 9:
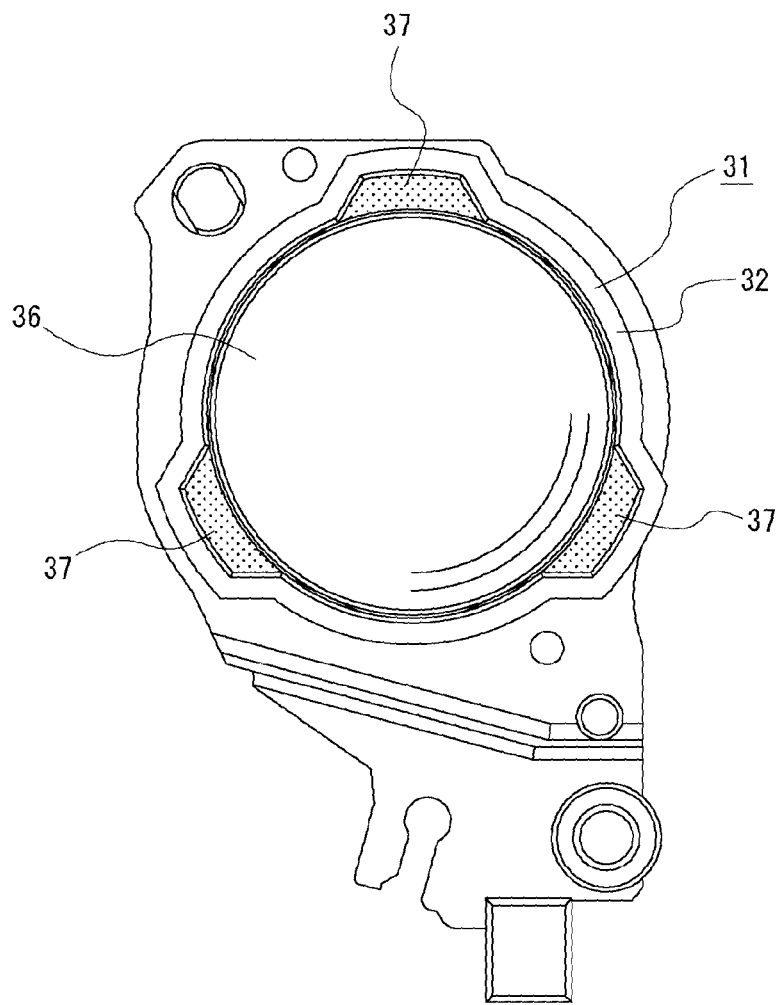
FIG. 9 is a front view in a state in which a focus lens is attached to the movable frame.

The focus lens 36 is attached to the lens holding portion 32 with adhesives 37 (see FIGS. 8 and 9). The adhesives 37 are made of a material which exhibits elasticity and whose bonding strength is less likely to decrease even under high temperature. Since the adhesives 37 are made of the material which exhibits elasticity and whose bonding strength is less likely to decrease even under high temperature, a difference in linear expansion between the movable frame 31 and the focus lens 36 is absorbed by the adhesives 37 when autoclaving for leaving the lens barrel 2 for about 10 minutes under a high temperature of equal to or higher than 100° C. is performed, for example. Thus, the focus lens 36 can be held on the lens holding portion 32 with high position accuracy, and damage of the focus lens 36 and dropping of the focus lens 36 from the lens holding portion 32 due to impact caused by, e.g., dropping can be prevented.

A biasing spring 38 and a nut member 39 arranged in the front-to-back direction are supported by the support shaft portion 34 (see FIGS. 6 and 7). The biasing spring 38 is, e.g., a torsion coil spring, and has the function of biasing the nut member 39 backward and biasing the nut member 39 toward one side in a direction about the axis of the support shaft portion 34. The nut member 39 is made of a resin material exhibiting both of high heat resistance and high sliding properties, such as polybutylene terephthalate (PBT). The nut member 39 includes a not-shown screwing protrusion screwed into a screw groove of the lead screw 30.

The nut member 39 is biased toward one side in the direction about the axis of the support shaft portion 34 by the biasing spring 38. In this manner, the screwing protrusion is screwed into the lead screw 30 with the screwing protrusion being laterally pushed against the lead screw 30.

As described above, the screwing protrusion of the nut member 39 is, by biasing force of the biasing spring 38, screwed into the lead screw 30 with the screwing protrusion being laterally pushed against the lead screw 30. Thus, even in a case where vibration etc. occur, it is less likely to unscrew the screwing protrusion from the lead screw 30, and the nut member 39 can be reliably screwed into the lead screw 30.

Moreover, the guide shafts 27 and the lead screw 30 are made of the metal materials, and the movable frame 31 and the nut member 39 are made of the resin materials. Thus, favorable slidability of the movable frame 31 relative to the guide shafts 27 is ensured while favorable slidability of the nut member 39 relative to the lead screw 30 is ensured upon rotation of the lead screw 30.

Thus, the movable frame 31 and the focus lens 36 can be smoothly and reliably moved in the optical axis direction.

Further, when autoclaving is performed, there is a probability that the position of the screwing protrusion with respect to the lead screw 30 changes due to a difference in a coefficient of linear expansion between the lead screw 30 made of the metal material and the nut member 39 made of the resin material. However, in this case, the screwing protrusion of the nut member 39 is also, by the biasing force of the biasing spring 38, screwed into the lead screw 30 with the screwing protrusion being laterally pushed against the lead screw 30. Thus, a favorable screwing state of the nut member 39 into the lead screw 30 can be ensured.

In addition, the nut member 39 is biased backward by the biasing spring 38. In this manner, the screwing protrusion is screwed into the screw groove of the lead screw 30 with the screwing protrusion being pushed against the screw groove from an axial direction of the lead screw 30. Thus, occurrence of backlash can be reduced.

When the lead screw 30 is rotated by drive force of the drive motor 29, the nut member 39 moves in a direction corresponding to a rotation direction of the lead screw 30, and then, the movable frame 31 is guided by the guide shafts 27 to move forward or backward together with the focus lens 36. In this manner, autofocusing is performed.

As described above, in the lens barrel 2, the movable frame 31 holding the focus lens 36 and being movable in the optical axis direction is made of the resin material. Thus, the weight of the movable frame 31 is reduced, and smooth movement of the movable frame 31 and weight reduction of the lens barrel 2 can be realized.

Moreover, autofocusing is performed in such a manner that the focus lens 36 moves in the optical axis direction in association with movement of the movable frame 31. Since autofocusing is performed by moving the lightweight movable frame 31, the operation speed of autofocusing is improved, and therefore, improvement in responsibility in focusing operation and improvement in focusing accuracy can be realized.

Further, the movable frame 31 is supported by the lead screw 30 as the drive shaft and the guide shafts 27, and the movable frame 31 and the focus lens 36 are, by the drive force transferred from the lead screw 30, guided and moved by the guide shafts 27.

Thus, direct acting type driving is performed, in which the movable frame 31 and the focus lens 36 are moved in the optical axis direction by the drive force transferred from the lead screw 30. Thus, the movable frame 31 and the focus lens 36 are moved with a simple configuration, and therefore, weight reduction of the lens barrel 2 and reduction of a manufacturing cost can be realized.

In a state in which the movable frame 31 is disposed in the housing 9, a portion of the movable frame 31 excluding part of the sleeve portion 35 is positioned in the internal space 11a, and part of the sleeve portion 35 and the drive motor 29 are positioned in the arrangement portion 19 (see FIG. 6). The arrangement portion 19 is a portion protruding backward from the lower end portion of the back surface portion 17 of the back cabinet 11. An arrangement space 40 is formed on the back side of the back surface portion 17 above the arrangement portion 19, and the element unit 8, a substrate, etc. are arranged in the arrangement space 40 as described later.

As described above, the arrangement space 40 is a space where the element unit 8 etc. as a configuration necessary for the lens barrel 2 are arranged. The arrangement portion 19 is provided below the arrangement space 40, and part of the sleeve portion 35 and the drive motor 29 are positioned in the arrangement portion 19. Thus, an effective space efficiency can be realized, and the size of the lens barrel 2 can be reduced.

Moreover, part of the sleeve portion 35 and the drive motor 29 are positioned on the back side with respect to the front cabinet 10. Thus, e.g., contact between the manual focus ring 5 rotatably supported by the front cabinet 10 and the drive motor 29 is avoided, and therefore, favorable operability of the manual focus ring 5 can be ensured while the size of the lens barrel 2 can be reduced.

Further, the size of the lens barrel 2 can be reduced, and therefore, the entire size of the medical observation device 100 can be also reduced. The practitioner can easily grasp the medical observation device 100 when the medical observation device 100 is used with the outer casing 1 being gripped by the practitioner, and therefore, gripping properties of the medical observation device 100 can be improved.

Note that the lens barrel 2 is configured such that the sleeve portion 35 and the drive motor 29 are positioned below the element unit 8. For this reason, the movable frame 31 is formed in a vertically-elongated shape (see FIGS. 8 and 9), and there is a probability that a weight balance of the movable frame 31 is deteriorated. However, the screwing protrusion of the nut member 39 is, by the biasing force of the biasing spring 38, screwed into the lead screw 30 with the screwing protrusion being laterally pushed against the lead screw 30. Thus, it is less likely to unscrew the screwing protrusion from the lead screw 30, and therefore, a favorable screwing state of the nut member 39 into the lead screw 30 can be ensured.

The element unit 8 is attached to the back surface portion 17 of the back cabinet 11, and is disposed in the arrangement space 40 (see FIGS. 3 to 6).

Figure 5:
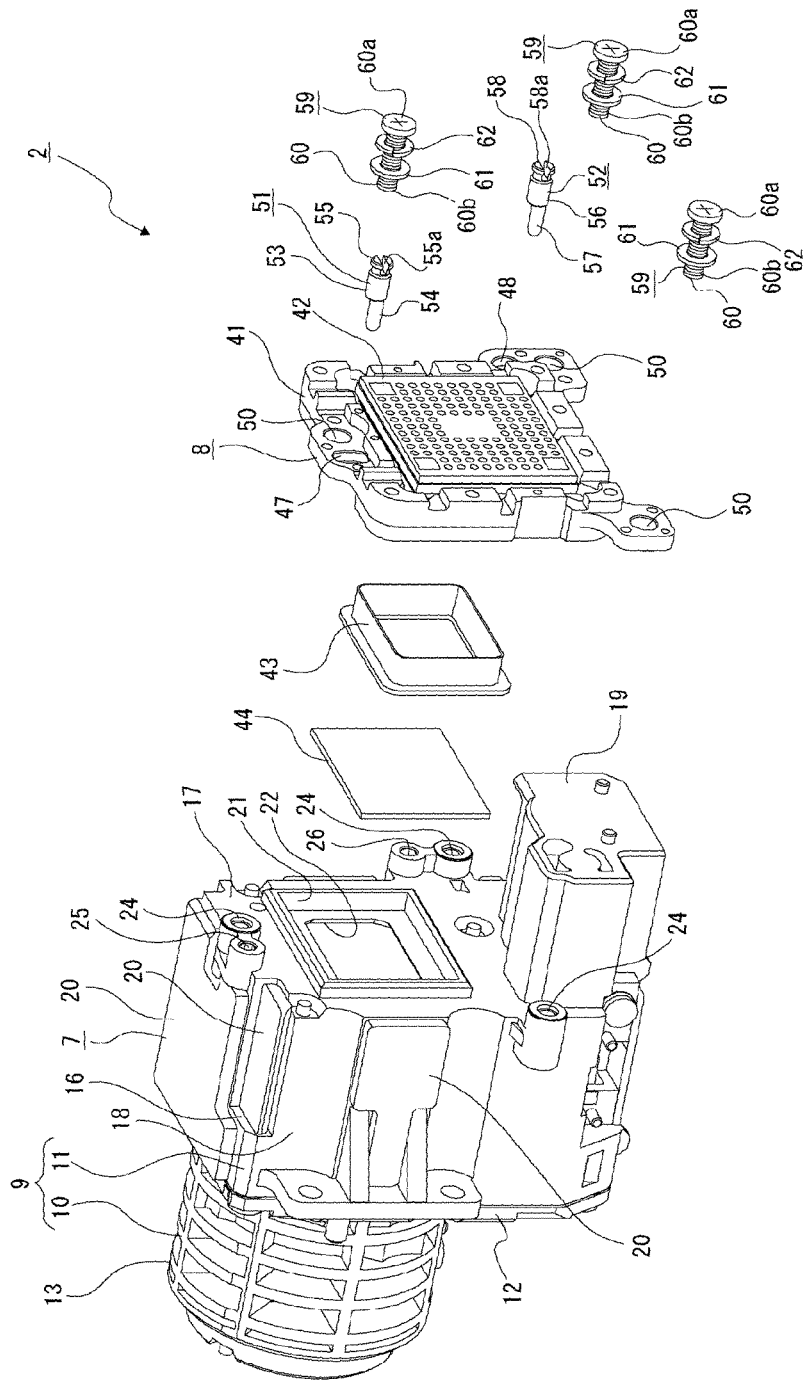
FIG. 5 is a perspective view of the lens barrel in a state in which a barrel unit and an element unit are detached from each other.
Figure 10:
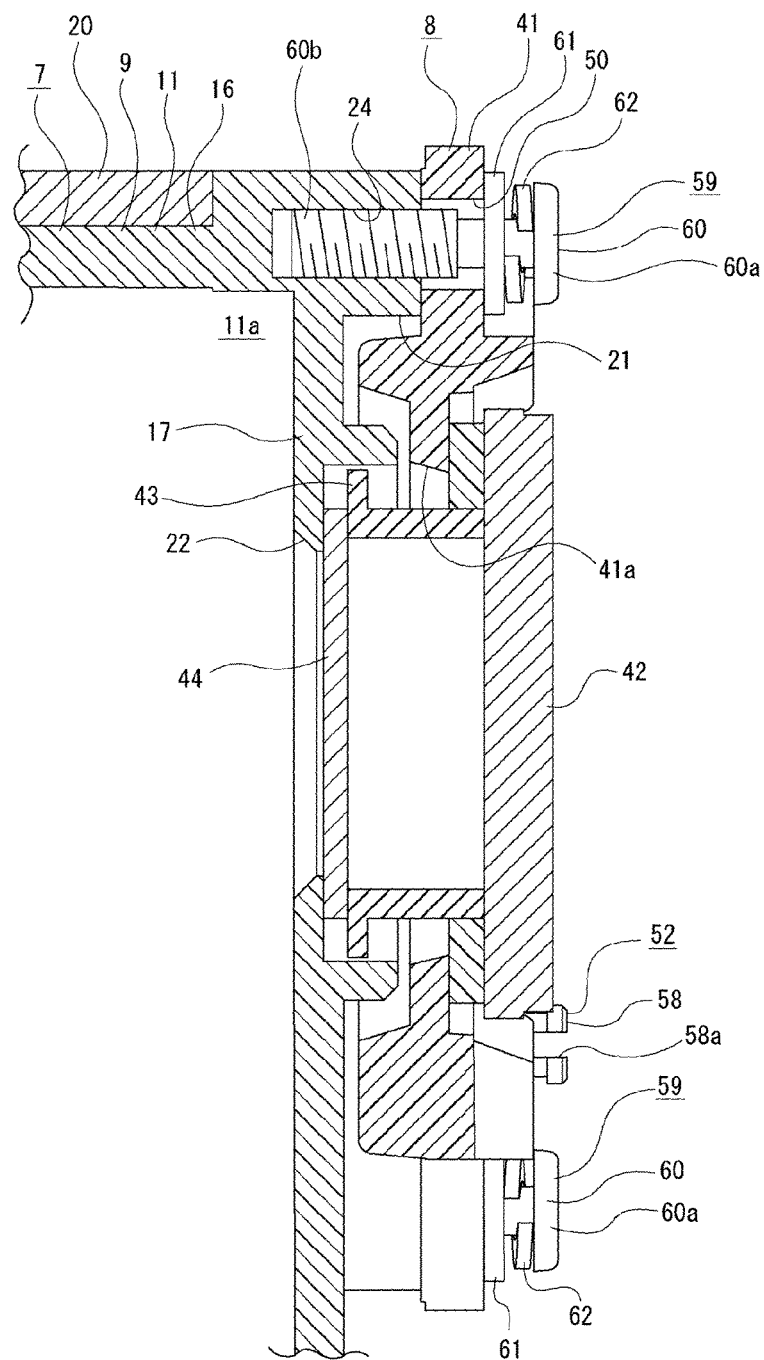
FIG. 10 is an enlarged cross-sectional view in a state in which the barrel unit and the element unit are linked together by attachment bodies.
Figure 11:
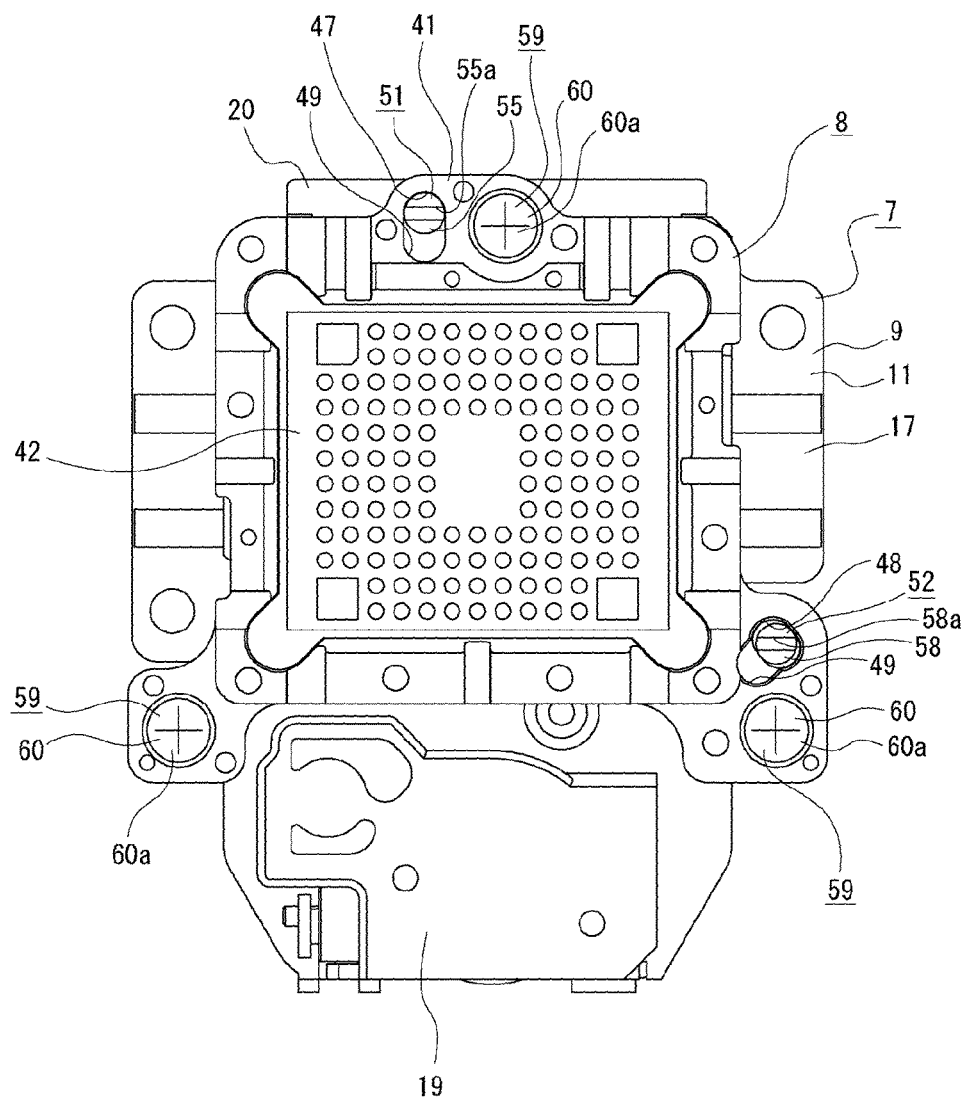
FIG. 11 is a back view of the lens barrel.

The element unit 8 includes an element holder 41 made of a resin material, and the imaging element 42 held with the imaging element 42 being attached to the element holder 41 with, e.g., an adhesive (see FIGS. 5, 10, and 11).

The element holder 41 is made of the resin material different from that of the housing 9 of the barrel unit 7, such as epoxy resin exhibiting excellent mechanical strength and high heat resistance. Thus, the element holder 41 and the housing 9 are different from each other in a coefficient of linear expansion. The element holder 41 is formed in a substantially rectangular frame shape, and an internal space of the element holder 41 is formed as a through-hole 41a.

The imaging element 42 is formed in a rectangular shape, and is attached to a back surface of the element holder 41 with, e.g., an epoxy-based adhesive with the imaging element 42 covering the through-hole 41a from the back side.

A sealing rubber 43 formed in a substantially rectangular frame shape is attached to a front surface of the imaging element 42, and an infrared cut filter 44 is attached to a front surface of the sealing rubber 43. The sealing rubber 43 is attached to the imaging element 42 with part of the sealing rubber 43 being inserted into the through-hole 41a, and adhesion of dust etc. to the imaging element 42 is prevented by the sealing rubber 43. The infrared cut filter 44 is positioned immediately on the back side of the transmission hole 22 formed at the back surface portion 17 of the back cabinet 11.

The substrate 45 is joined to a back surface of the imaging element 42 by, e.g., reflow (see FIG. 6). For example, the substrate 45 is configured such that two rigid substrates exhibiting high stiffness are connected together by a flexible wiring board disposed with the flexible wiring board being folded between the rigid substrates.

A flexible printed wiring board 46 is connected to the substrate 45. The flexible printed wiring board 46 is configured such that each portion thereof is bent (see FIGS. 3, 4, and 6). Each portion is attached to, e.g., a back surface of the arrangement portion 19, a lower surface of the lens holding portion 13 of the front cabinet 10, etc., and is connected to a corresponding one of necessary portions. The flexible printed wiring board 46 is disposed with part of the flexible printed wiring board 46 being folded in the arrangement space 40, and a tip end portion of the folded portion is connected to the substrate 45.

A cable inserted into the insertion hole 4a formed at the cover body 4 of the outer casing 1 is connected to the flexible printed wiring board 46, and power is supplied from an external power supply to each portion via the cable and the flexible printed wiring board 46, for example.

As described above, the substrate 45 is, by reflow, joined to the imaging element 42 in the element unit 8. Thus, the element unit 8 is exposed to high temperature in a reflow furnace. However, the element holder 41 is made of the resin material exhibiting high heat resistance, and therefore, the element unit 8 is sufficiently adapted to reflow. Consequently, a favorable joint state of the substrate 45 to the imaging element 42 can be ensured without, e.g., deformation of the element holder 41.

Moreover, the epoxy-based adhesive used for attachment of the imaging element 42 to the element holder 41 also exhibits high heat resistance, and therefore, detachment of the imaging element 42 from the element holder 41 is not caused even upon reflow. Consequently, a favorable attachment state by bonding of the imaging element 42 to the element holder 41 can be ensured.

Further, the element holder 41 is made of the resin material exhibiting high compatibility with the epoxy-based adhesive used for attachment of the imaging element 42, and therefore, high bonding strength is obtained by the epoxy-based adhesive. Consequently, a favorable bonding state of the imaging element 42 to the element holder 41 can be ensured.

A first pin insertion through-hole 47 and a second pin insertion through-hole 48 both penetrating the element holder 41 in the front-to-back direction are formed at the element holder 41 (see FIG. 5). The first pin insertion through-hole 47 is formed in a circular shape, and is positioned at a center portion of an upper end portion of the element holder 41 in the right-to-left direction, for example. The second pin insertion through-hole 48 is formed in an elongated-hole shape, and is positioned at one side portion of the element holder 41 below the first pin insertion through-hole 47, for example. The second pin insertion through-hole 48 is formed such that a longitudinal direction thereof is along a direction connecting between the first pin insertion through-hole 47 and the second pin insertion through-hole 48.

The diameter of the first pin insertion through-hole 47 is larger than that of the first pin insertion hole 25 formed at the back surface portion 17 of the back cabinet 11, and the diameter (the width) of the second pin insertion through-hole 48 is larger than that of the second pin insertion hole 26 formed at the back surface portion 17 of the back cabinet 11.

Adhesive reservoir recessed portions 49 opening on the back side are formed at the element holder 41, and are continuously positioned respectively at the first pin insertion through-hole 47 and the second pin insertion through-hole 48.

Screw insertion holes 50 are formed to penetrate an outer peripheral portion of the element holder 41 in the front-to-back direction.

The element unit 8 is linked to the barrel unit 7 by position adjustment using a first eccentric pin 51 and a second eccentric pin 52.

Figure 12:
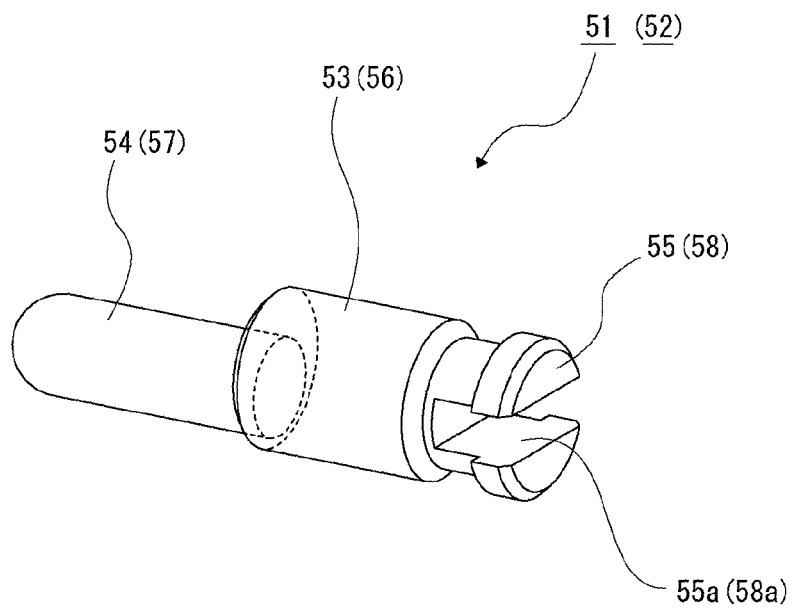
FIG. 12 is an enlarged perspective view of an eccentric pin.

As illustrated in FIG. 12, the first eccentric pin 51 includes a circular-columnar insertion shaft portion 53 extending in the front-to-back direction, an eccentric shaft portion 54 protruding forward from a front surface of the insertion shaft portion 53, and an operation target portion 55 protruding backward from a back surface of the insertion shaft portion 53. An operation slit 55a is formed at the operation target portion 55. The eccentric shaft portion 54 is positioned eccentric with respect to the insertion shaft portion 53, and the center axis of the eccentric shaft portion 54 is shifted with respect to the center axis of the insertion shaft portion 53.

Figure 13:
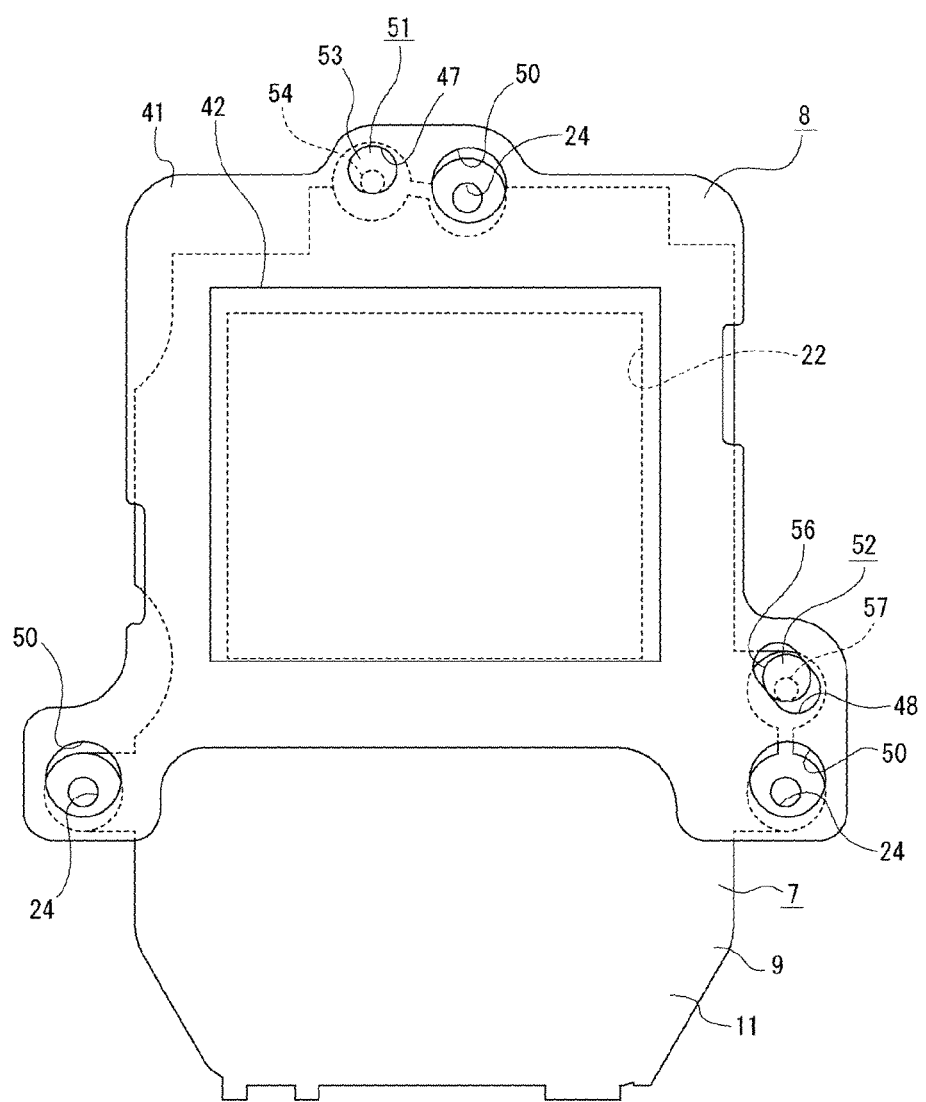
FIG. 13 is a schematic back view in a state before positioning of the barrel unit and the element unit is made.

The first eccentric pin 51 is inserted such that the insertion shaft portion 53 is inserted into the first pin insertion through-hole 47 from the back side and that the eccentric shaft portion 54 is inserted into the first pin insertion hole 25 from the back side (see FIG. 13). Note that in each of FIGS. 13, 14, 15, and 17, e.g., the positions of the screw holes 24 and the screw insertion holes 50 are exaggeratingly illustrated as a greatly-shifted state for the sake of easy understanding of description. The insertion shaft portion 53 and the eccentric shaft portion 54 are rotatably fitted respectively into the first pin insertion through-hole 47 and the first pin insertion hole 25.

As illustrated in FIG. 12, the second eccentric pin 52 includes a circular-columnar insertion shaft portion 56 extending in the front-to-back direction, an eccentric shaft portion 57 protruding forward from a front surface of the insertion shaft portion 56, and an operation target portion 58 protruding backward from a back surface of the insertion shaft portion 56. An operation slit 58a is formed at the operation target portion 58. The eccentric shaft portion 57 is positioned eccentric with respect to the insertion shaft portion 56, and the center axis of the eccentric shaft portion 57 is shifted with respect to the center axis of the insertion shaft portion 56.

The eccentric amount of the eccentric shaft portion 54 with respect to the insertion shaft portion 53 of the first eccentric pin 51 is the same as that of the eccentric shaft portion 57 with respect to the insertion shaft portion 56 of the second eccentric pin 52.

The second eccentric pin 52 is inserted such that the insertion shaft portion 56 is inserted into the second pin insertion through-hole 48 from the back side and that the eccentric shaft portion 57 is inserted into the second pin insertion hole 26 from the back side (see FIG. 13). The insertion shaft portion 56 is rotatably inserted into the second pin insertion through-hole 48, and the eccentric shaft portion 57 is rotatably fitted into the second pin insertion hole 26.

Figure 14:
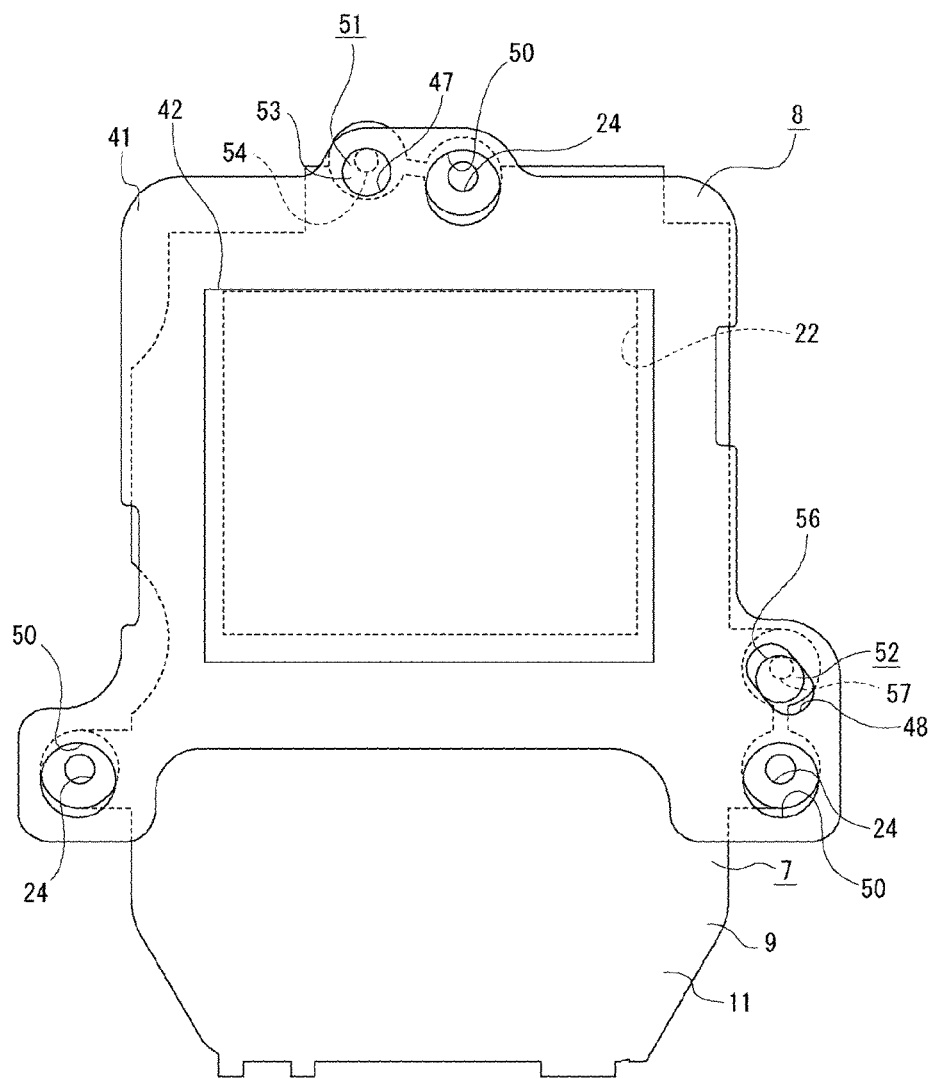
FIG. 14 is a schematic back view in a state in which positioning of the barrel unit and the element unit is made.

In a state in which the first eccentric pin 51 is inserted into the first pin insertion through-hole 47 and the first pin insertion hole 25 and the second eccentric pin 52 is inserted into the second pin insertion through-hole 48 and the second pin insertion hole 26, the first eccentric pin 51 or the second eccentric pin 52 is rotated such that the position of the element unit 8 with respect to the barrel unit 7 is adjusted (see FIG. 14). The first eccentric pin 51 and the second eccentric pin 52 are each rotated by rotation of a not-shown jig, such as a screwdriver, inserted into each of the operation slits 55a, 58a.

The position of the element unit 8 with respect to the barrel unit 7 is adjusted such that the optical axis of the imaging optical system of the barrel unit 7 and the center (the middle) of the imaging element 42 of the element unit 8 are coincident with each other. Such position adjustment is performed while the position of the barrel unit 7 and the position of the element unit 8 displayed on the monitor are being observed.

For example, when the first eccentric pin 51 is rotated, the insertion shaft portion 53 rotates about the eccentric shaft portion 54 as a pivot point in an eccentric state. Then, the position of the first pin insertion through-hole 47 with respect to the first pin insertion hole 25 changes, and the position of the element unit 8 with respect to the barrel unit 7 changes. In this state, the second eccentric pin 52 rotates about the eccentric shaft portion 57 as a pivot point in association with rotation of the first eccentric pin 51.

On the other hand, when the second eccentric pin 52 is rotated, the insertion shaft portion 56 rotates about the eccentric shaft portion 57 as a pivot point in an eccentric state. Then, the position of the second pin insertion through-hole 48 with respect to the second pin insertion hole 26 changes, and the position of the element unit 8 with respect to the barrel unit 7 changes. In this state, the first eccentric pin 51 rotates about the eccentric shaft portion 54 as a pivot point in association with rotation of the second eccentric pin 52.

As described above, the first eccentric pin 51 or the second eccentric pin 52 is rotated such that the position of the element unit 8 with respect to the barrel unit 7 changes, and adjustment of the position of the element unit 8 with respect to the barrel unit 7 is terminated when the optical axis of the imaging optical system and the center of the imaging element 42 become coincident with each other.

In adjustment of the positions of the barrel unit 7 and the element unit 8 as described above, the first eccentric pin 51 and the second eccentric pin 52 are used, the eccentric amount of the eccentric shaft portion 54 with respect to the insertion shaft portion 53 being the same as the eccentric amount of the eccentric shaft portion 57 with respect to the insertion shaft portion 56.

Thus, the same eccentric pins may be used as the first eccentric pin 51 and the second eccentric pin 52. Consequently, the positions of the barrel unit 7 and the element unit 8 can be easily adjusted while the manufacturing cost of the lens barrel 2 can be reduced.

Moreover, since the positions of the barrel unit 7 and the element unit 8 are adjusted, it is not necessary to preset, considering position shift between the imaging optical system and the imaging element 42, a smaller imaging area of the imaging element 42 as compared to an effective imaging area of the imaging element 42, and an image quality can be improved using the entirety of the effective imaging area of the imaging element 42 without the imaging area extending outside the effective imaging area.

Figure 15:
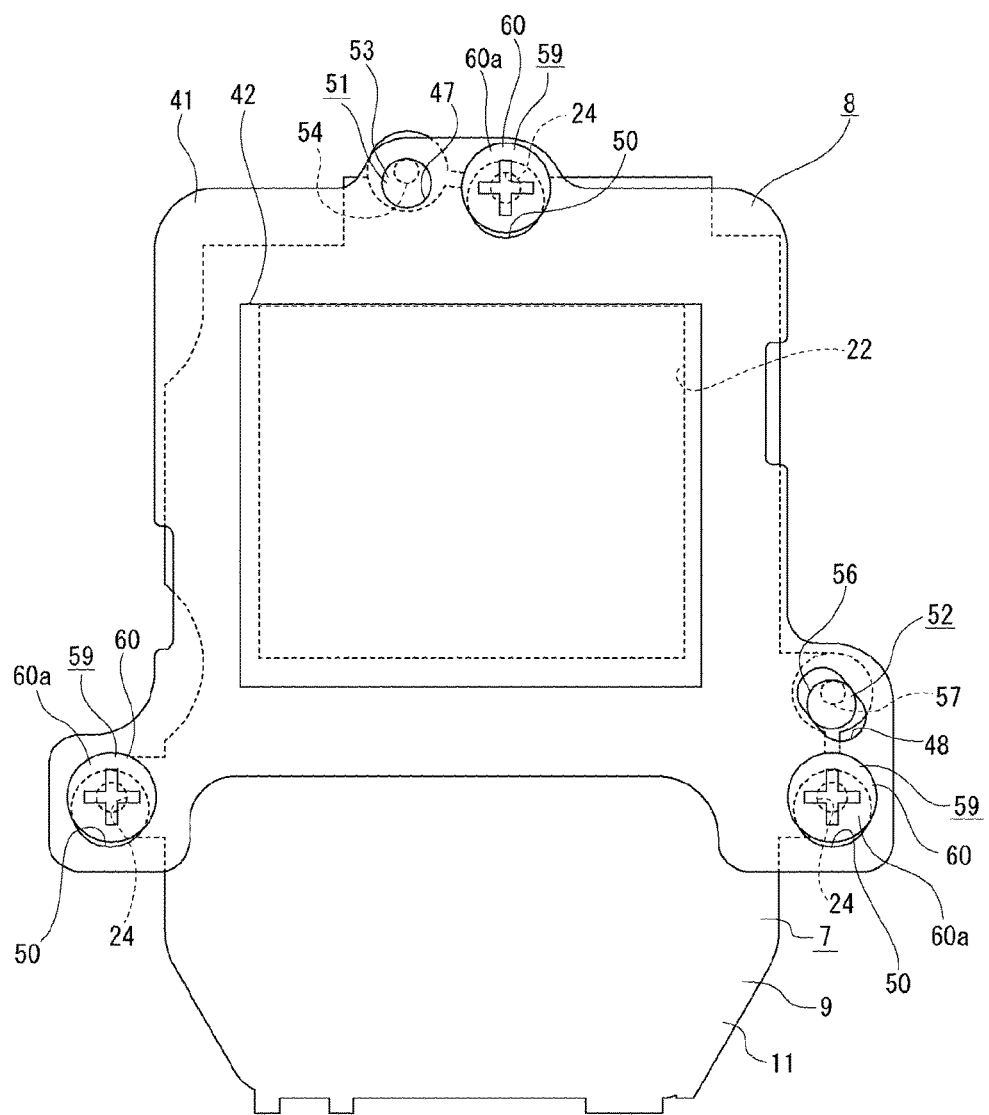
FIG. 15 is a schematic back view in a state in which positioning of the barrel unit and the element unit is made and the barrel unit and the element unit are linked together by the attachment bodies.

When adjustment of the position of the element unit 8 with respect to the barrel unit 7 is terminated, the barrel unit 7 and the element unit 8 are linked together by attachment bodies 59 (see FIGS. 10, 11, and 15).

When the barrel unit 7 and the element unit 8 are linked together by the attachment bodies 59, a not-shown adhesive is applied to each adhesive reservoir recessed portion 49, and the first eccentric pin 51 and the second eccentric pin 52 are fixed to the element holder 41. The first eccentric pin 51 and the second eccentric pin 52 are fixed to the element holder 41 with the adhesive applied to each adhesive reservoir recessed portion 49, and therefore, dropping of the first eccentric pin 51 and the second eccentric pin 52 from the element holder 41 is prevented.

Note that the adhesive applied to each adhesive reservoir recessed portion 49 is an adhesive rich in elasticity. Such an adhesive expands/contracts when the element holder 41 moves relative to the first eccentric pin 51 and the second eccentric pin 52 within a certain area, thereby preventing detachment of the element holder 41 from the first eccentric pin 51 and the second eccentric pin 52.

Figure 16:
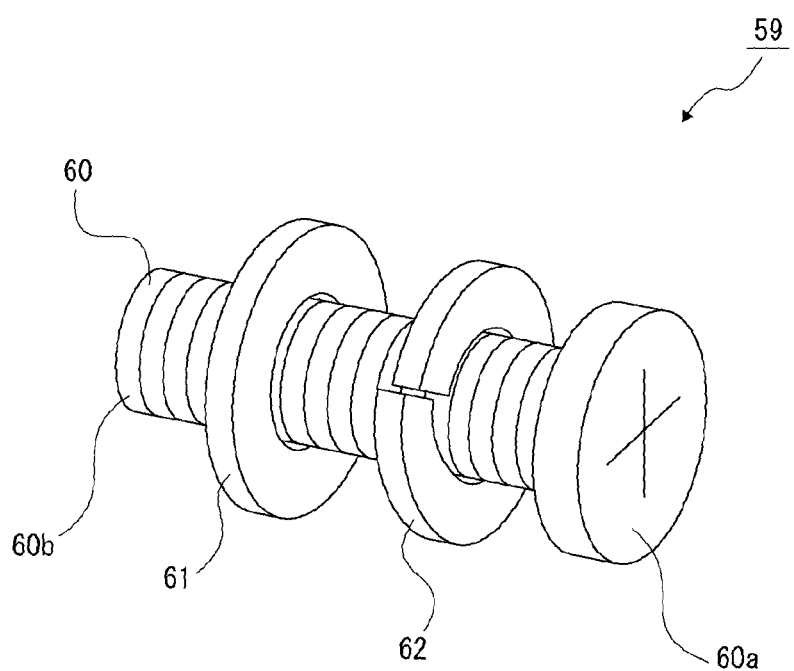
FIG. 16 is an enlarged perspective view of the attachment body.
Figure 17:
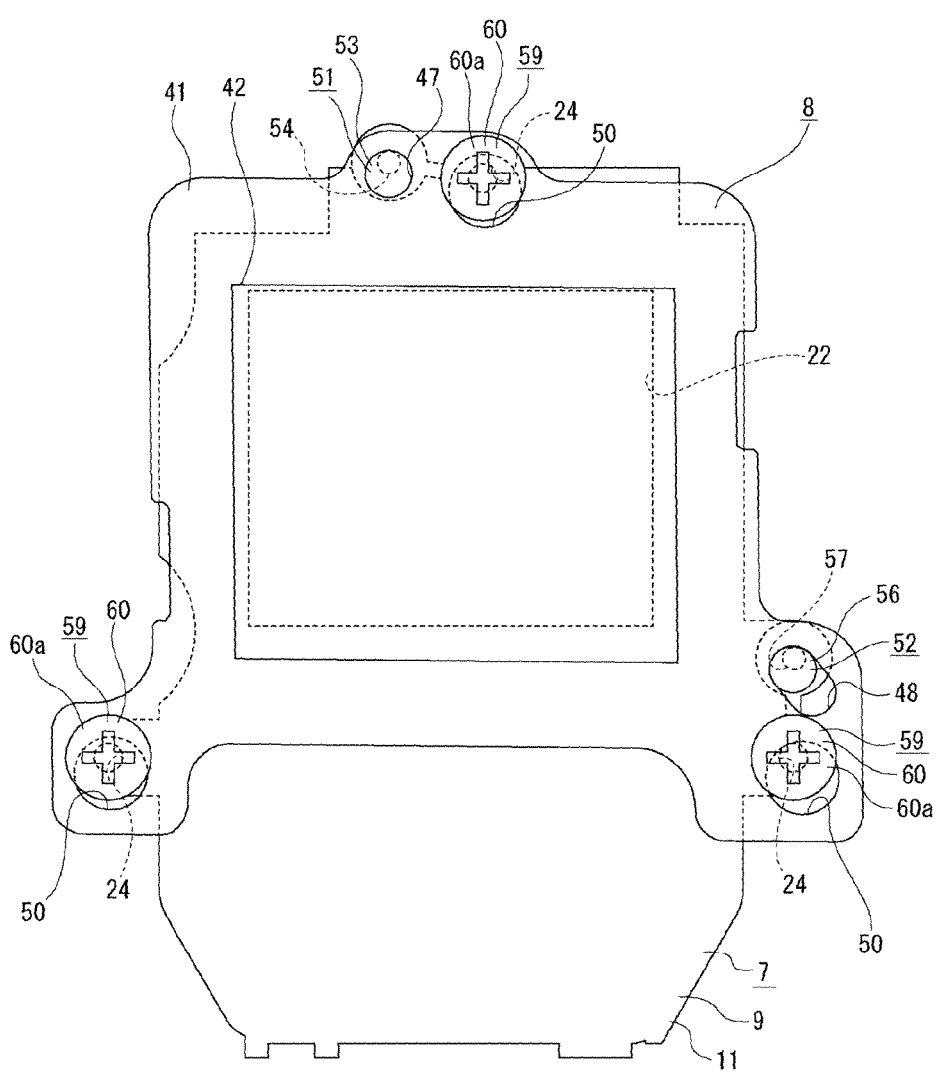
FIG. 17 is a schematic back view in a state in which the element unit is displaced relative to the barrel unit due to expansion or contraction.

The attachment body 59 includes a fastening screw 60, a retainer plate 61, and a retainer spring 62 (see FIG. 16).

The fastening screw 60 includes a head portion 60a with a rotation operation groove, and a threaded shaft portion 60b protruding from the head portion 60a. The threaded shaft portion 60b is inserted into the screw insertion hole 50 of the element holder 41, and the diameter of the screw insertion holes 50 is larger than that of the threaded shaft portion 60b.

The retainer plate 61 is formed in a ring shape, and the threaded shaft portion 60b of the fastening screw 60 is inserted into the retainer plate 61. Thus, the retainer plate 61 is movable relative to the threaded shaft portion 60b in an axial direction of the threaded shaft portion 60b.

The retainer spring 62 is, e.g., a washer-shaped spring, and is disposed between the head portion 60a of the fastening screw 60 and the retainer plate 61 with the retainer spring 62 being supported by the threaded shaft portion 60b. The retainer spring 62 has the function of biasing the retainer plate 61 in a direction apart from the head portion 60a in the axial direction of the threaded shaft portion 60b.

As illustrated in FIG. 10, the threaded shaft portion 60b of the fastening screw 60 of each attachment body 59 is inserted into a corresponding one of the screw insertion holes 50 of the element holder 41 from the back side, and is screwed into a corresponding one of the screw holes 24 formed at the back surface portion 17 of the back cabinet 11. The threaded shaft portion 60b is screwed into the screw hole 24 such that the barrel unit 7 and the element unit 8 are linked together with positioning of the barrel unit 7 and the element unit 8 being made and that part of a front surface of the element holder 41 contacts part of a back surface of the barrel unit 7. In a state in which the barrel unit 7 and the element unit 8 are linked together, part of the element unit 8 is disposed in the arrangement recessed portion 21 of the back surface portion 17.

Note that in a state in which positioning of the barrel unit 7 and the element unit 8 is made, there is a probability that the position of each screw insertion hole 50 is shifted with respect to the position of a corresponding one of the screw holes 24 in a plane perpendicular to the optical axis direction. However, the fastening screw 60 is provided as a tapping screw. Thus, even in a case where the position of each screw insertion hole 50 is shifted with respect to the position of a corresponding one of the screw holes 24, the fastening screws 60 are screwed into the back surface portion 17, and therefore, the barrel unit 7 and the element unit 8 can be linked together without changing a position relationship between the barrel unit 7 and the element unit 8.

As described above, it is configured such that each fastening screw 60 is provided as the tapping screw and is screwed into the back surface portion 17. Thus, the screw holes 24 may be, without forming the screw holes 24 at the back surface portion 17 in advance, formed in such a manner that the fastening screws 60 are screwed into the back surface portion 17, or may be formed in such a manner that each fastening screw 60 is screwed into a hole formed in advance at the back surface portion 17 and having a smaller diameter than that of the threaded shaft portion 60b.

As described above, in the lens barrel 2, the barrel unit 7 and the element unit 8 are, in the optical axis direction, linked together by the fastening screws 60 in a state in which positioning of the barrel unit 7 and the element unit 8 is made by the first eccentric pin 51 and the second eccentric pin 52.

Thus, the barrel unit 7 and the element unit 8 are linked together by the fastening screws 60 with a positioning state of the barrel unit 7 and the element unit 8 being held, and detachment of the barrel unit 7 and the element unit 8 can be prevented in the positioning state.

In a state in which the barrel unit 7 and the element unit 8 are linked together by the attachment bodies 59, the retainer plates 61 contact the back surface of the element holder 41. The retainer plate 61 is, by the retainer spring 62, biased in the direction apart from the head portion 60a. Thus, the element holder 41 is pushed from the back side by the retainer plates 61, and closely contacts the back surface portion 17.

In this state, a change in external environment might be caused due to, e.g., autoclaving, and the housing 9 and the element holder 41 might expand or contract in the front-to-back direction. However, in this case, the retainer springs 62 elastically deform to absorb the change amount of the dimensions of the housing 9 or the element holder 41 due to expansion or contraction, and therefore, a favorable linking state of the barrel unit 7 and the element unit 8 is held.

As described above, the retainer spring 62 for pushing the element unit 8 against the barrel unit 7 is supported on the fastening screw 60, and therefore, the element unit 8 is pushed against the barrel unit 7 by the retainer springs 62 with the barrel unit 7 and the element unit 8 being linked together by the fastening screws 60.

Thus, the retainer springs 62 expand/contract when the barrel unit 7 or the element unit 8 expands or contracts due to the change in external environment, and therefore, a favorable linking state of the barrel unit 7 and the element unit 8 can be ensured even in a state in which the barrel unit 7 or the element unit 8 expands or contracts.

Moreover, when the change in external environment is caused due to, e.g., autoclaving, the housing 9 and the element holder 41 might expand or contract even in the plane perpendicular to the optical axis direction. In this case, due to a difference in a coefficient of linear expansion between the housing 9 and the element holder 41, the element unit 8 displaces relative to the barrel unit 7 in the plane perpendicular to the optical axis direction (see FIG. 17).

In this state, the element unit 8 displaces relative to the barrel unit 7 with reference to the eccentric shaft portion 54 of the first eccentric pin 51, and the position of the elongated-hole-shaped second pin insertion through-hole 48 changes with respect to the insertion shaft portion 56 of the second eccentric pin 52. As described above, the second pin insertion through-hole 48 is formed in the elongated-hole shape, and therefore, displacement of the element unit 8 relative to the barrel unit 7 is allowed.

Thus, when one of the barrel unit 7 or the element unit 8 displaces relative to the other one of the barrel unit 7 or the element unit 8 due to expansion or contraction of the barrel unit 7 or the element unit 8 caused by the external environment, displacement of the barrel unit 7 or the element unit 8 according to the change in external environment is allowed, and therefore, distortion or deformation of the barrel unit 7 and the element unit 8 can be prevented.

Moreover, since displacement of the barrel unit 7 and the element unit 8 is allowed, the housing 9 and the element holder 41 can be each made of an optimal material for ensuring necessary performance. Consequently, functionality of the barrel unit 7 and the element unit 8 can be improved while favorable performance can be ensured.

Further, the housing 9 and the element holder 41 can be made of the optimal materials, considering heat resistance, strength, a cost, etc. Thus, functionality of the barrel unit 7 and the element unit 8 can be improved while the manufacturing cost of the lens barrel 2 can be reduced.

Note that the lens barrel 2 is, as described above, configured such that the longitudinal direction of the elongated-hole-shaped second pin insertion through-hole 48 is along the direction connecting between the first pin insertion through-hole 47 and the second pin insertion through-hole 48. Thus, when the element unit 8 displaces relative to the barrel unit 7 with reference to the eccentric shaft portion 54 of the first eccentric pin 51 inserted into the first pin insertion through-hole 47, the insertion shaft portion 56 of the second eccentric pin 52 is less likely to interfere with displacement of the element unit 8, and therefore, the element unit 8 can smoothly displace relative to the barrel unit 7.

As described above, the diameter of each screw insertion hole 50 of the element holder 41 is larger than that of a corresponding one of the threaded shaft portions 60*b* of the fastening screws 60.

Since the diameter of the screw insertion hole 50 is larger than that of the threaded shaft portion 60*b* as described above, the threaded shaft portion 60*b* displaces relative to the screw insertion hole 50 when the barrel unit 7 or the element unit 8 expands or contracts in a direction perpendicular to the optical axis direction due to the external environment. Thus, the threaded shaft portion 60*b* does not contact the relatively-displaced element unit 8.

Thus, a favorable linking state of the barrel unit 7 and the element unit 8 is ensured while relative displacement of the barrel unit 7 and the element unit 8 is allowed. Consequently, distortion or deformation of the barrel unit 7 and the element unit 8 can be prevented.

When the external environment returns to original environment after, e.g., termination of autoclaving, the expanded or contracted barrel unit 7 and the element unit 8 return to original states, and return to original positioning states before the change in external environment.

As described above, in the lens barrel 2, the housing 9 of the barrel unit 7 is made of the resin material, and the element holder 41 of the element unit 8 is made of the material different from that of the housing 9.

Thus, the housing 9 in which the imaging optical system is disposed is made of the resin material, and the element holder 41 for holding the imaging element 42 is made of the material different from that of the housing 9. Consequently, weight reduction can be realized while favorable performance of the imaging element 42 can be ensured.

In particular, the medical observation device 100 is gripped by the practitioner upon use, and therefore, practitioner's usability can be improved by weight reduction.

Moreover, the housing 9 and the element holder 41 are both made of the resin materials. Thus, the housing 9 and the element holder 41 can be easily formed in desired shapes as compared to metal materials, and the degree of freedom in designing can be improved. In addition, the housing 9 can be formed in the minimum possible size and shape according to the structure positioned in the housing 9, and therefore, size reduction can be realized.

Further, since the housing 9 and the element holder 41 are both made of the resin materials, manufacturing cost reduction can be realized.

[One Embodiment of Medical Observation Device]

Figure 18:
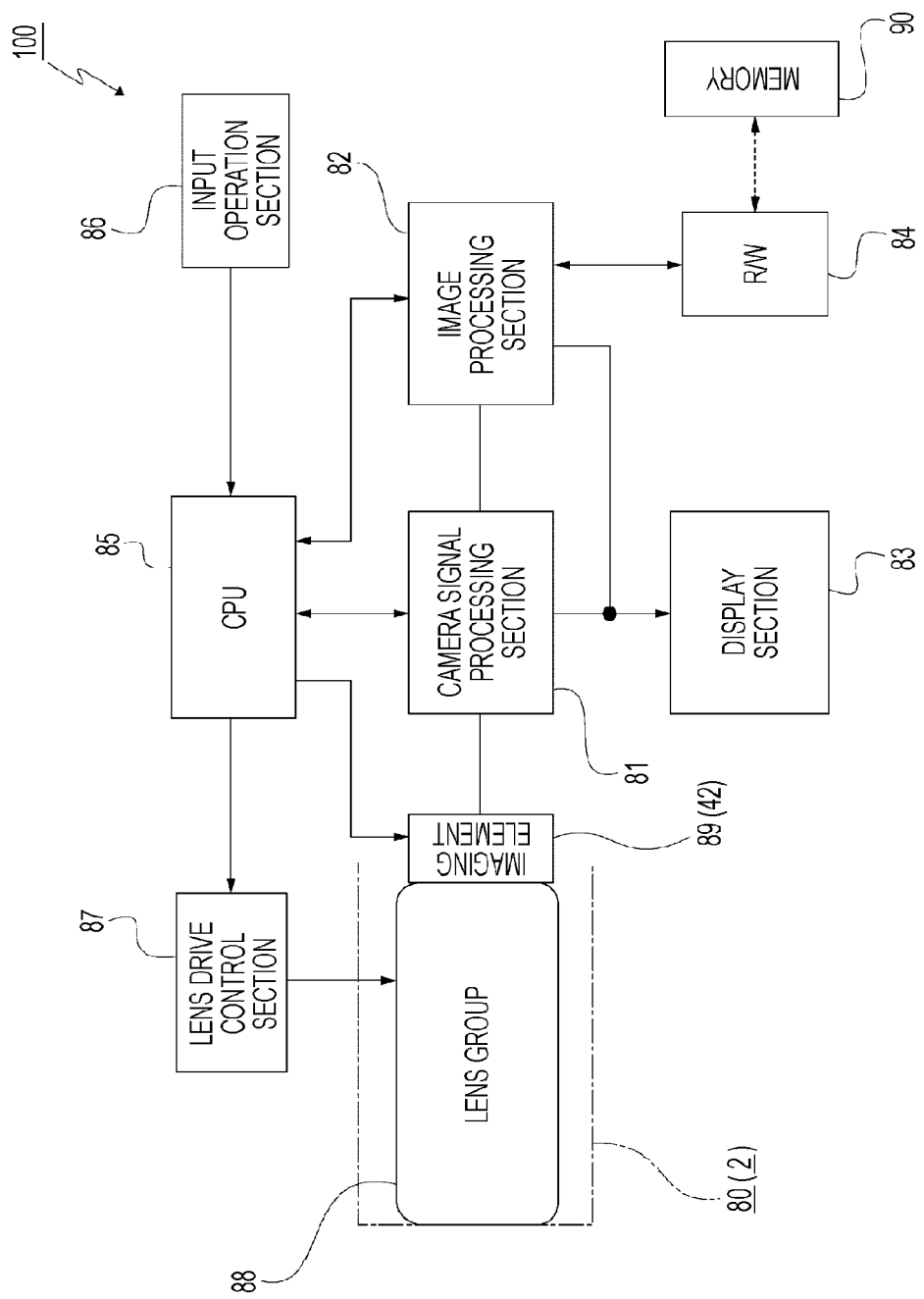
FIG. 18 is a block diagram of one example of the medical observation device.

FIG. 18 illustrates a block diagram of one embodiment of the medical observation device of the present technology.

A medical observation device 100 includes a lens barrel 80 (the lens barrel 2) having an imaging function, a camera signal processing section 81 configured to perform signal processing such as analog-to-digital conversion of a shot image signal, and an image processing section 82 configured to perform the processing of recording and reproducing the image signal. Moreover, the medical observation device 100 includes a display section 83 configured to display, e.g., a shot image, a reader/writer (R/W) 84 configured to write the image signal in a memory 90 and read the image signal from the memory 90, a central processing unit (CPU) 85 configured to control the entirety of the medical observation device 100, an input operation section 86 such as various switches for which desired operation is made by a user, and a lens drive control section 87 configured to control driving of lenses arranged in the lens barrel 80.

The lens barrel 80 includes, for example, an imaging optical system having a lens group 88 (lenses 14 and a focus lens 36), and an imaging element 89 (an imaging element 42) such as a charge coupled device (CCD) or a complementary metal-oxide semiconductor (CMOS).

The camera signal processing section 81 is configured to perform various types of signal processing such as conversion of an output signal of the imaging element 89 into a digital signal, noise removal, image quality correction, and conversion into a brightness/color-difference signal.

The image processing section 82 is configured to perform, e.g., compression coding processing or expansion decoding processing of the image signal based on a predetermined image data format and the processing of converting data specifications such as a definition.

The display section 83 has the function of displaying various types of data such as the state of operation for the input operation section 86 by the user and the shot image. Note that the display section 83 is not necessarily provided at the medical observation device 100, and the medical observation device 100 may be configured such that an image is displayed after shot image data has been sent to other display units such as a monitor.

The R/W 84 is configured to write the image data encoded by the image processing section 82 in the memory 90 and read the image data recorded in the memory 90.

The CPU 85 functions as a control processing section configured to control each circuit block provided at the medical observation device 100, and is configured to control each circuit block on the basis of, e.g., an instruction input signal from the input operation section 86.

The input operation section 86 is configured to output the instruction input signal corresponding to user's operation to the CPU 85.

The lens drive control section 87 is configured to control, on the basis of a control signal from the CPU 85, a drive source (the drive motor 29) configured to drive the lens (the focus lens 36) of the lens group 88.

The memory 90 is a semiconductor memory detachable from a slot connected to the R/W 84, for example.

Operation of the medical observation device 100 will be described below.

In a shooting standby state, an image signal shot by the lens barrel 80 is output to the display section 83 via the camera signal processing section 81 under the control of the CPU 85, and is displayed as a camera-through image. Moreover, when the instruction input signal for focusing is input from the input operation section 86, the CPU 85 outputs the control signal to the lens drive control section 87, and a predetermined lens of the lens group 88 is moved on the basis of control of the lens drive control section 87.

When shooting is performed by the instruction input signal from the input operation section 86, the shot image signal is output from the camera signal processing section 81 to the image processing section 82, and the compression encoding processing is performed for such a signal. Then, the resultant is converted into digital data in a predetermined data format. The converted data is output to the R/W 84, and is written in the memory 90.

Focusing is performed in such a manner that the lens drive control section 87 moves the focus lens 36 of the lens group 88 on the basis of the control signal from the CPU 85.

In a case where the image data recorded in the memory 90 is reproduced, predetermined image data is read from the memory 90 by the R/W 84 according to the operation for the input operation section 86. After the expansion decoding processing has been performed by the image processing section 82, a reproduction image signal is output to the display section 83, and a reproduction image is displayed.

[Present Technology]

The present technology may have the following configurations.

(1)

A lens barrel of a medical observation device, including:
a barrel unit including an imaging optical system configured to acquire an image of an object, and a housing in which the imaging optical system is disposed; and
an element unit including an imaging element configured to photoelectrically convert the image of the object acquired by the imaging optical system, and an element holder configured to hold the imaging element,
in which the housing is made of a resin material, and the element holder is made of a material different from that of the housing.

(2)

The lens barrel of the medical observation device according to (1), in which
one or more lenses are provided at the imaging optical system,
a movable frame is provided, which is configured to hold at least one of the lenses and move in an optical axis direction, and
the movable frame is made of a resin material.

(3)

The lens barrel of the medical observation device according to (2), in which
autofocusing is performed in such a manner that the at least one of the lenses held by the movable frame is moved in the optical axis direction in association with movement of the movable frame.

(4)

The lens barrel of the medical observation device according to (1) or (2), further including:
a drive shaft whose axial direction is along the optical axis direction; and
a guide shaft disposed parallel to the drive shaft,
in which the movable frame is supported by the drive shaft and the guide shaft, and
the movable frame is, using drive force transferred from the drive shaft, guided and moved by the guide shaft.

(5)

The lens barrel of the medical observation device according to any of (1) to (4), further including:
at least two eccentric pins for positioning of the barrel unit and the element unit in a plane perpendicular to the optical axis direction,
in which at least two pin insertion holes are formed at the barrel unit,
at least two pin insertion through-holes are formed at the element unit,
a portion of each eccentric pin is inserted into a corresponding one of the pin insertion holes, and another portion of each eccentric pin is inserted into a corresponding one of the pin insertion through-holes,
at least one of the eccentric pins is rotated in a direction about an axis such that a position of the element unit with respect to the barrel unit is adjusted, and
at least one of the pin insertion through-holes is formed in an elongated-hole shape.

(6)

The lens barrel of the medical observation device according to (5), in which
each eccentric pin includes an insertion shaft portion to be inserted into a corresponding one of the pin insertion through-hole, and an eccentric shaft portion which is to be inserted into a corresponding one of the pin insertion holes and which is provided eccentric with respect to the insertion shaft portion, and
an eccentric amount of the eccentric shaft portion with respect to the insertion shaft portion is identical among all of the eccentric pins.

(7)

The lens barrel of the medical observation device according to (5) or (6), in which
in a state in which positioning of the barrel unit and the element unit is made by the eccentric pins,
the barrel unit and the element unit are, in the optical axis direction, linked together with a fastening screw.

(8)

The lens barrel of the medical observation device according to (7), in which
a retainer spring configured to push the element unit against the barrel unit is supported on the fastening screw.

(9)

The lens barrel of the medical observation device according to (8), in which
a screw hole into which the fastening screw is to be screwed is formed at the barrel unit,
a screw insertion hole into which the fastening screw is to be inserted is formed at the element unit, and
a diameter of the screw insertion hole is larger than that of the fastening screw.

(10)

A medical observation device including:
a barrel unit including an imaging optical system configured to acquire an image of an object, and a housing in which the imaging optical system is disposed; and
an element unit including an imaging element configured to photoelectrically convert the image of the object acquired by the imaging optical system, and an element holder configured to hold the imaging element,
in which the housing is made of a resin material, and
the element holder is made of a material different from that of the housing.

REFERENCE SIGNS LIST

100 Medical observation device
2 Lens barrel
7 Barrel unit
8 Element unit
9 Housing
14 Lens
24 Screw hole
25 First pin insertion hole
26 Second pin insertion hole
27 Guide shaft
30 Lead screw (drive shaft)
31 Movable frame
36 Focus lens
41 Element holder
42 Imaging element
47 First pin insertion through-hole
48 Second pin insertion through-hole
50 Screw insertion hole
51 First eccentric pin
52 Second eccentric pin
53 Insertion shaft portion
54 Eccentric shaft portion
56 Insertion shaft portion
57 Eccentric shaft portion
60 Fastening screw
62 Retainer spring
80 Lens barrel
89 Imaging element

The invention claimed is:

1. A lens barrel of a medical observation device, comprising:
a barrel unit including an imaging optical system configured to acquire an image of an object, and a housing in which the imaging optical system is disposed;
an element unit including an imaging element configured to photoelectrically convert the image of the object acquired by the imaging optical system, and an element holder configured to hold the imaging element,
wherein the housing is made of a resin material, and
the element holder is made of a material different from that of the housing;
at least two eccentric pins for positioning of the barrel unit and the element unit in a plane perpendicular to the optical axis direction,
wherein at least two pin insertion holes are formed at the barrel unit,
at least two pin insertion through-holes are formed at the element unit,
a portion of each eccentric pin is inserted into a corresponding one of the pin insertion holes, and another portion of each eccentric pin is inserted into a corresponding one of the pin insertion through-holes,
at least one of the eccentric pins is rotated in a direction about an axis such that a position of the element unit with respect to the barrel unit is adjusted, and
at least one of the pin insertion through-holes is formed in an elongated-hole shape.

2. The lens barrel of the medical observation device according to claim 1, wherein
one or more lenses are provided at the imaging optical system,
a movable frame is provided, which is configured to hold at least one of the lenses and move in an optical axis direction, and
the movable frame is made of a resin material.

3. The lens barrel of the medical observation device according to claim 2, wherein
autofocusing is performed in such a manner that the at least one of the lenses held by the movable frame is moved in the optical axis direction in association with movement of the movable frame.

4. The lens barrel of the medical observation device according to claim 2, further comprising:
a drive shaft whose axial direction is along the optical axis direction; and
a guide shaft disposed parallel to the drive shaft,
wherein the movable frame is supported by the drive shaft and the guide shaft, and
the movable frame is, using drive force transferred from the drive shaft, guided and moved by the guide shaft.

5. The lens barrel of the medical observation device according to claim 1, wherein
each eccentric pin includes an insertion shaft portion to be inserted into a corresponding one of the pin insertion through-hole, and an eccentric shaft portion which is to be inserted into a corresponding one of the pin insertion holes and which is provided eccentric with respect to the insertion shaft portion, and
an eccentric amount of the eccentric shaft portion with respect to the insertion shaft portion is identical among all of the eccentric pins.

6. The lens barrel of the medical observation device according to claim 1, wherein
in a state in which positioning of the barrel unit and the element unit is made by the eccentric pins,
the barrel unit and the element unit are, in the optical axis direction, linked together with a fastening screw.

7. The lens barrel of the medical observation device according to claim 6, wherein
a retainer spring configured to push the element unit against the barrel unit is supported on the fastening screw.

8. The lens barrel of the medical observation device according to claim 7, wherein a screw hole into which the fastening screw is to be screwed is formed at the barrel unit,
a screw insertion hole into which the fastening screw is to be inserted is formed at the element unit, and
a diameter of the screw insertion hole is larger than that of the fastening screw.

9. A medical observation device comprising:
a barrel unit including an imaging optical system configured to acquire an image of an object, and a housing in which the imaging optical system is disposed;
an element unit including an imaging element configured to photoelectrically convert the image of the object acquired by the imaging optical system, and an element holder configured to hold the imaging element,
wherein the housing is made of a resin material, and
the element holder is made of a material different from that of the housing;
at least two eccentric pins for positioning of the barrel unit and the element unit in a plane perpendicular to the optical axis direction,
wherein at least two pin insertion holes are formed at the barrel unit,
at least two pin insertion through-holes are formed at the element unit,
a portion of each eccentric pin is inserted into a corresponding one of the pin insertion holes, and another portion of each eccentric pin is inserted into a corresponding one of the pin insertion through-holes,
at least one of the eccentric pins is rotated in a direction about an axis such that a position of the element unit with respect to the barrel unit is adjusted, and
at least one of the pin insertion through-holes is formed in an elongated-hole shape.

* * * * *